United States Patent
Bernotas et al.

(10) Patent No.: US 7,585,876 B2
(45) Date of Patent: Sep. 8, 2009

(54) AZAINDOLYLALKYLAMINE DERIVATIVES AS 5-HYDROXYTRYPTAMINE-6 LIGANDS

(75) Inventors: Ronald Charles Bernotas, Royersford, PA (US); Derek Cecil Cole, New City, NY (US); William Joseph Lennox, South Plainfield, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/941,479

(22) Filed: Nov. 16, 2007

(65) Prior Publication Data

US 2008/0114023 A1    May 15, 2008

Related U.S. Application Data

(63) Continuation of application No. 10/922,678, filed on Aug. 19, 2004, now Pat. No. 7,297,705, which is a continuation of application No. 10/323,263, filed on Dec. 19, 2002, now Pat. No. 6,800,640.

(60) Provisional application No. 60/342,838, filed on Dec. 20, 2001.

(51) Int. Cl.
*A01N 43/42* (2006.01)
*A61K 31/44* (2006.01)
(52) U.S. Cl. .................................... 514/300
(58) Field of Classification Search .................. 514/300
See application file for complete search history.

(56) References Cited

U.S. PATENT DOCUMENTS

| | | | |
|---|---|---|---|
| 5,977,131 A | 11/1999 | Nagel | |
| 6,100,291 A | 8/2000 | Slassi et al. | |
| 6,187,805 B1 | 2/2001 | Pineiro et al. | |
| 6,476,034 B2 | 11/2002 | Wang et al. | |
| 6,770,642 B2 * | 8/2004 | Cole et al. | 514/233.2 |
| 2006/0128744 A1 * | 6/2006 | Schechter et al. | 514/300 |

FOREIGN PATENT DOCUMENTS

| | | |
|---|---|---|
| WO | WO 00/63203 A1 | 10/2000 |
| WO | WO 01/12629 A1 | 2/2001 |

OTHER PUBLICATIONS

Yoshioka et al., Life sciences, (1998) vol. 62, No. 17-18, pp. 1473-1477.*
J. Mérour et al, Reactions of Substituted 2,3-Dihydro-1H-indol-3-ones and Pyrrolo[2,3-b]pyridin-3-ones with Wittig and Horner-Emmons Reagents: Synthesis of 7-Azatryptamine, Tetrahedron 57 (2001) 1995-2002.

D. Mazéas et al, Synthesis of New Melatoninergic Ligands Including Azaindole Moiety, Heterocycles 50 (1999) 1065-1080.
M. Hichour et al, Synthesisi of 4,5-Disubstituted-2-piperidinones from 4-Piperidinones, Heterocyclic Communications 4 (1998) 71-76.
Adell et al. "Strategies for producing faster acting antidepressants" Drug Discovery Today 2005 10(8):578-585.
Hayes et al. "The effects of 5HT$_1$ agonists on erection in rats in vivo and rabbit corpus cavernosum in vitro" International Journal of Impotence Research 2002 14(4):205-212.
Kwon et al. "List of drugs in development in Neurodegenerative Disease" Neurodegenerative Dis. 2004 1:113-152.
Matsumoto et al. "5HT2a and muscarinic receptors in schizophrenia: a postmortem study" Neuroscience Letters 2005 379:164-168.
Meneses, Alfredo "Effects of the 5-HT6 receptor antagonist Ro 04-6790 on learning consolidation" Behavioural Brain ResearchVolume 2001 118(1):107-110.
Miguel-Hidalgo, J. J. "SB-271046 SmithKlein Beecham" Curr Opin Investig Drugs. Jan. 2001;2(1):118-22.
Mitchell et al. "5-HT6 Receptors: A Novel Target for Cognitive Enhancement" Pharm. & Ther. 2005 108:320-333.
Russell, M. G. N. et al. "*N*-Arylsulfonylindole Derivatives as Serotonin 5-HT$_6$ Receptor Ligands" J. Med. Chem. 2001 44(23):3881-3895.
Schechter et al. "The potential utility of 5HT1a Receptor Antagonists in the Treatment of Cognitive Dysfunction Associated with Alzheimer's Disease" Curr. Pharm. Des. 2002 8(2) abstract.
Slassi, Abdelmalik et al. "Recent progress in 5-HT$_6$ receptor antagonists for the treatment of CNS diseases" Expert Opinion on Therapeutic Patents, 2002 12(4):513-527.

* cited by examiner

*Primary Examiner*—D. Margaret Seaman
*Assistant Examiner*—Niloofar Rahmani
(74) *Attorney, Agent, or Firm*—Gloria K. Szakiel; Scott K. Larsen; David R. Kurlandsky

(57) ABSTRACT

The present invention provides a compound of formula I and the use thereof for the therapeutic treatment of disorders relating to or affected by the 5-HT6 receptor.

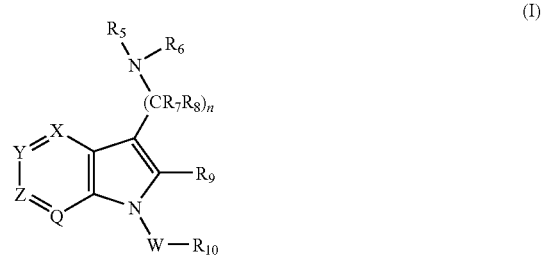

(I)

6 Claims, No Drawings

AZAINDOLYLALKYLAMINE DERIVATIVES AS 5-HYDROXYTRYPTAMINE-6 LIGANDS

This application is a continuation of application Ser. No. 10/922,678, filed Aug. 19, 2004, which is a continuation of application Ser. No. 10/323,263, filed Dec. 19, 2002, which claims the benefit of U.S. Provisional Application No. 60/342,838, filed Dec. 20, 2001, the entire disclosure each of which is hereby incorporated by reference.

BACKGROUND OF THE INVENTION

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia or bulimia), neurodegenerative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides an indolylalkylamine derivative of formula I

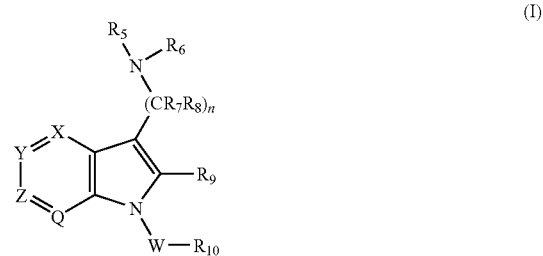

(I)

wherein
W is $SO_2$, CO, $CONR_{11}$ or $CSNR_{12}$;
X is N or $CR_1$;
Y is N or $CR_2$;
Z is N or $CR_3$;
Q is N or $CR_4$ with the proviso that no more than two of X, Y, Z and Q may be N;
n is an integer of 2 or 3;
$R_1$, $R_2$, $R_3$ and $R_4$ are each independently H, halogen, CN, $OCO_2R_{13}$, $CO_2R_{14}$, $CONR_{15}R_{16}$, $CNR_{17}NR_{18}R_{19}$, $SO_mR_{20}$, $NR_{21}R_{22}$, $OR_{23}$, $COR_{24}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_5$ and $R_6$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;
$R_7$ and $R_8$ are each independently H or an optionally substituted $C_1$-$C_6$alkyl group;
$R_9$ is H, halogen, or a $C_1$-$C_6$alkyl, $C_1$-$C_6$alkoxy, aryl or heteroaryl group each optionally substituted;
$R_{10}$ is an optionally substituted $C_1$-$C_6$alkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S with the proviso that when Q is N and X, Y and Z are CH then $R_{10}$ must be other than phenyl;
m is 0 or an integer of 1 or 2;
$R_{11}$ and $R_{12}$ are each independently H or a $C_1$-$C_6$alkyl, aryl or heteroaryl group each optionally substituted;
$R_{13}$, $R_{14}$, $R_{20}$, $R_{23}$ and $R_{24}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{15}$ and $R_{16}$ are each independently H or an optionally substituted $C_1$-$C_6$alkyl group; and
$R_{17}$, $R_{18}$, $R_{19}$, $R_{21}$ and $R_{22}$ are each independently H or an optionally substituted $C_1$-$C_4$alkyl group; or $R_{21}$ and $R_{22}$ may be taken together with the atom to which they are attached to form a 5- to 7-membered ring optionally containing another heteroatom selected from O, N or S; or the stereoisomers thereof or the pharmaceutically acceptable salts thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd.

Surprisingly, it has now been found that azaindolylalkylamine derivatives of formula I demonstrate 5-HT6 affinity. Advantageously, said amine derivatives may be used as effective therapeutic agents for the treatment of central nervous system (CNS) disorders associated with or affected by the 5-HT6 receptor. Accordingly, the present invention provides azaindolylalkylamine derivatives of formula I

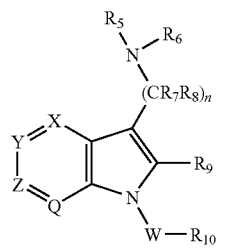

(I)

wherein

W is $SO_2$, CO, $CONR_{11}$ or $CSNR_{12}$;

X is N or $CR_1$;

Y is N or $CR_2$;

Z is N or $CR_3$;

Q is N or $CR_4$ with the proviso that no more than two of X, Y, Z and Q may be N;

n is an integer of 2 or 3;

$R_1$, $R_2$, $R_3$ and $R_4$ are each independently H, halogen, CN, $OCO_2R_{13}$, $CO_2R_{14}$, $CONR_{15}R_{16}$, $CNR_{17}NR_{18}R_{19}$, $SO_mR_{20}$, $NR_{21}R_{22}$, $OR_{23}$, $COR_{24}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_5$ and $R_6$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;

$R_7$ and $R_8$ are each independently H or an optionally substituted $C_1$-$C_6$alkyl group;

$R_9$ is H, halogen, or a $C_1$-$C_6$alkyl, $C_1$-$C_6$alkoxy, aryl or heteroaryl group each optionally substituted;

$R_{10}$ is an optionally substituted $C_1$-$C_6$alkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S with the proviso that when Q is N and X, Y and Z are CH then $R_{10}$ must be other than phenyl;

m is 0 or an integer of 1 or 2;

$R_{11}$ and $R_{12}$ are each independently H or a $C_1$-$C_6$alkyl, aryl or heteroaryl group each optionally substituted;

$R_{13}$, $R_{14}$, $R_{20}$, $R_{23}$ and $R_{24}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{15}$ and $R_{16}$ and are each independently H or an optionally substituted $C_1$-$C_6$alkyl group; and $R_{17}$, $R_{18}$, $R_{19}$, $R_{21}$ and $R_{22}$ are each independently H or an optionally substituted $C_1$-$C_4$alkyl group; or $R_{21}$ and $R_{22}$ may be taken together with the atom to which they are attached to form a 5- to 7-membered ring optionally containing another heteroatom selected from O, N or S; or the stereoisomers thereof or the pharmaceutically acceptable salts thereof.

As used in the specification and claims, the term halogen designates Br, Cl, I or F and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $W_1$ is NR, O or S; and R is H or an optional substituent as described hereinbelow:

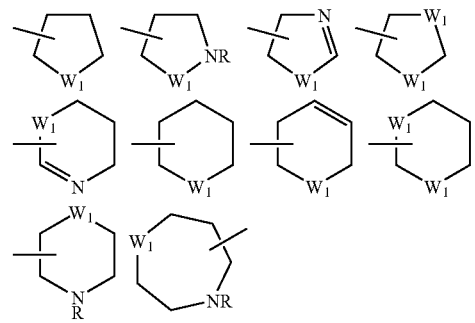

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a five- to ten-membered carbocyclic aromatic ring system such as phenyl, naphthyl, or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at a bridgehead and optionally containing 1, 2 or 3 additional heteroatoms selected from N, O or S included in the term as designated herein are the following ring systems wherein $W_2$ is NR, O or S; and R is H or an optional substituent as described hereinbelow:

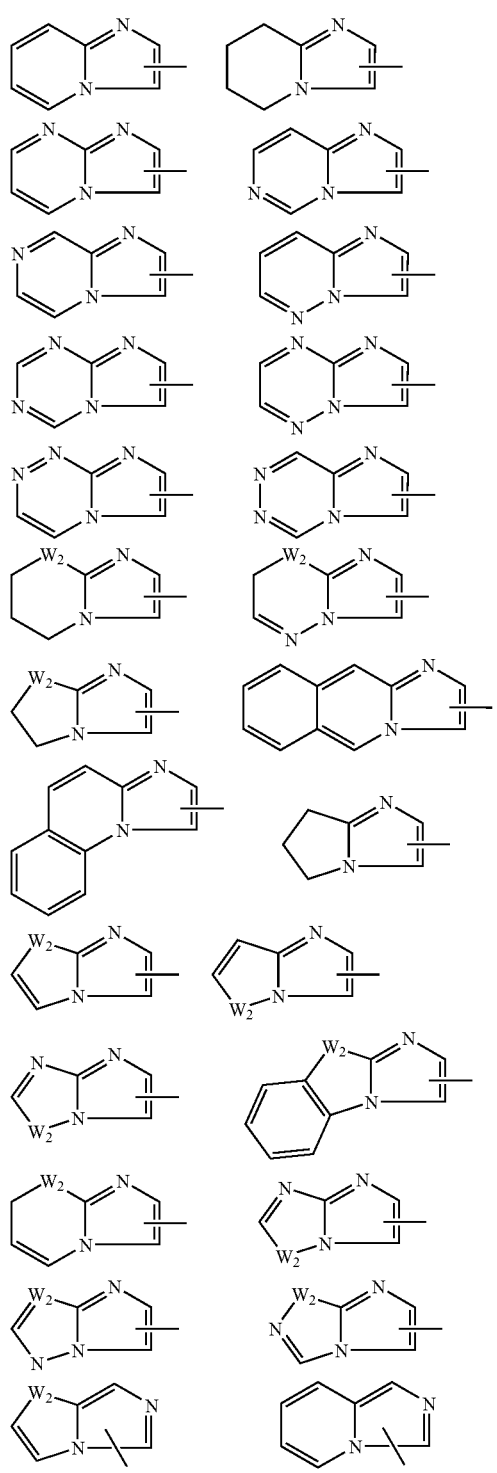

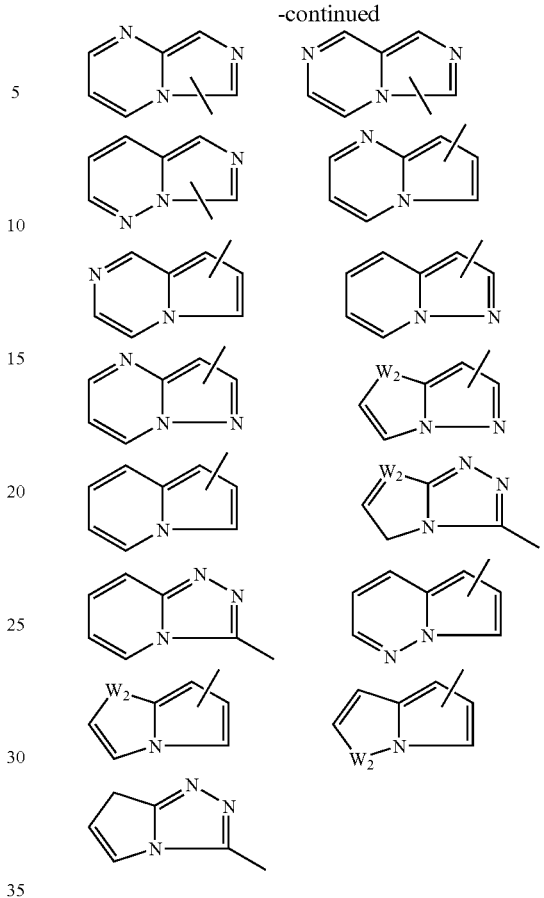

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl, heteroaryl or 8- to 13-membered bicyclic or tricyclic ring system having a N atom at the bridgehead are designated as being optionally substituted, the substituent groups which are optionally present may be one or more, e.g., two or three, the same or different, of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heteroaryl, cycloheteroalkyl or cycloalkyl groups, preferably halogen atoms or lower alkyl groups. Typically, 0-3 substituents, the same or different, may be present. When any of the foregoing substituents represents or contains an alkyl substituent group e.g. alkoxy, alkanoyl or the like, this may be linear and branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

Preferred compounds of the invention are those compounds of formula I wherein W is $SO_2$. Also preferred are those compounds of formula I wherein n is 2. Another group of preferred compounds of formula I are those compounds wherein X is N; Y is $CR_2$; Z is $CR_3$; and Q is $CR_4$. Yet another group of preferred compounds of the invention are those compounds of formula I wherein Q is N; X is $CR_1$; Y is $CR_2$; and Z is $CR_3$.

More preferred compounds of the invention are those compounds of formula I wherein W is $SO_2$ and $R_9$ is H. Another group of more preferred compounds are those compounds of formula I wherein W is $SO_2$; n is 2; and $R_9$ is H. Further more preferred compounds are those formula I compounds wherein W is $SO_2$; n is 2; $R_9$ is H; and X is N; Y is $CR_2$; Z is $CR_3$; Q is $CR_4$; and $R_2$, $R_3$ and $R_4$ are each independently H, halogen or lower alkyl. Yet another group of more preferred compounds of formula I are those compounds wherein W is $SO_2$; n is 2; $R_9$ is H; and Q is N; X is $CR_1$; Y is $CR_2$; Z is $CR_3$; and $R_1$, $R_2$, and $R_3$ are each independently H, halogen or lower alkyl.

Preferred compounds of the invention include:
2-[1-(2-chlorobenzenesulfonyl)-1H-pyrrolo[3,2-b]pyridin-3-yl]ethylamine;
2-[1-(2-naphthylsulfonyl)-1H-pyrrolo[3,2-b]pyridin-3-yl]ethylamine;
2-{1-[(3-trifluoromethyl)benzenesulfonyl]-1H-pyrrolo[3,2-b]pyridin-3-yl}ethylamine;
2-{1-{[2-chloro-4-(trifluoromethyl)benzene]sulfonyl}-1H-pyrrolo[3,2-b]pyridin-3-yl}ethylamine;
2-{1-[(3,4-difluorobenzene)sulfonyl]-1H-pyrrolo[3,2-b]pyridin-3-yl}ethylamine;
2-{1-[(3-chlorobenzene)sulfonyl]-1H-pyrrolo[3,2-b]pyridin-3-yl}ethylamine;
2-{1-[(5-chlorothiophen-2-yl)sulfonyl]-1H-pyrrolo[3,2-b]pyridin-3-yl}ethylamine;
2-{1-[(6-chloroimidazo[2,1-b]thiazol-5-yl)sulfonyl]-1H-pyrrolo[3,2-b]pyridin-3-yl}ethylamine;
2-{1-[(3-methoxybenzene)sulfonyl]-1H-pyrrolo[3,2-b]pyridin-3-yl}ethylamine;
2-{1-[(imidazo[2,1-b]thiazol-5-yl)sulfonyl]-1H-pyrrolo[3,2-b]pyridin-3-yl}ethylamine;
2-[1-(benzenesulfonyl)-1H-pyrrolo[3,2-b]pyridin-3-yl]-ethylamine;
2-{1-[(3-fluorobenzene)sulfonyl]-1H-pyrrolo[3,2-b]pyridin-3-yl}ethylamine;
2-{1-[(4-aminobenzene)sulfonyl]-1H-pyrrolo[3,2-b]pyridin-3-yl}ethylamine;
2-{1-[(3-methyl benzene)sulfonyl]-1H-pyrrolo[3,2-b]pyridin-3-yl}ethylamine;
2-{1-[(2,3-dichlorobenzene)sulfonyl]-1H-pyrrolo[3,2-b]pyridin-3-yl}ethylamine;
2-{1-[(2-fluorobenzene)sulfonyl]-1H-pyrrolo[3,2-b]pyridin-3-yl}ethylamine;
2-{1-[(3-bromobenzene)sulfonyl]-1H-pyrrolo[3,2-b]pyridin-3-yl}ethylamine;
2-{1-(2,6-dichloroimidazo[2,1-b]thiazol-5-yl)sulfonyl]-1H-pyrrolo[3,2-b]pyridin-3-yl}ethylamine;
2-{1-(6-chloroimidazo[2,1-b]thiazol-5-yl)sulfonyl]-1H-pyrrolo[3,2-c]pyridin-3-yl}ethylamine;
2-{1-(imidazo[2,1-b]thiazol-5-yl)sulfonyl]-1H-pyrrolo[3,2-c]pyridin-3-yl}ethylamine;
2-{1-[(3-chlorobenzene)sulfonyl]-1H-pyrrolo[3,2-c]pyridin-3-yl}ethylamine;
2-{1-[(3-fluorobenzene)sulfonyl]-1H-pyrrolo[3,2-c]pyridin-3-yl}ethylamine;
2-{1-[(3-methoxybenzene)sulfonyl]-1H-pyrrolo[3,2-c]pyridin-3-yl}ethylamine;
2-{1-[(5-chlorothiophen-2-yl)sulfonyl]-1H-pyrrolo[3,2-c]pyridin-3-yl}ethylamine;
2-[1-(benzenesulfonyl)-1H-pyrrolo[3,2-c]pyridin-3-yl]ethylamine;
2-{1-[(3-methyl benzene)sulfonyl]-1H-pyrrolo[3,2-c]pyridin-3-yl}ethylamine;
2-{1-{[(3-trifluoromethyl)benzene]sulfonyl}-1H-pyrrolo[3,2-c]pyridin-3-yl}ethylamine;
2-{1-[(2,3-dichlorobenzene)sulfonyl]-1H-pyrrolo[3,2-c]pyridin-3-yl}ethylamine;
{2-{1-(benzo[1,2,5]thiadiazol-4-yl)sulfonyl]-1H-pyrrolo[3,2-c]pyridin-3-yl}ethyl}dimethylamine;
{2-{1-[(7-chlorobenzo[1,2,5]oxadiazol-4-yl)sulfonyl]-1H-pyrrolo[3,2-c]pyridin-3-yl}ethyl}dimethylamine;
{2-{1-[(6-chloroimidazo[2,1-b]thiazol-5-yl)sulfonyl]-1H-pyrrolo[3,2-c]pyridin-3-yl}ethyl}dimethylamine;
{2-{1-[(5-chloro-3-methyl benzo[b]thiophen-2-yl)sulfonyl]-1H-pyrrolo[3,2-c]pyridin-3-yl}ethyl}dimethylamine;
2-{1-[(3-methoxybenzene)sulfonyl]-1H-pyrrolo[2,3-c]pyridin-3-yl}ethylamine;
2-{1-[(1-methyl-1H-imidazol-4-yl)sulfonyl]-1H-pyrrolo[2,3-c]pyridin-3-yl}ethylamine;
2-{1-[(3,5-dimethylisoxazol-4-yl)sulfonyl]-1H-pyrrolo[2,3-c]pyridin-3-yl}ethylamine;
2-{1-[(2,4-difluorobenzene)sulfonyl]-1H-pyrrolo[2,3-c]pyridin-3-yl}ethylamine;
{2-{1-[(5-chlorothiophen-2-yl)sulfonyl]-1H-pyrrolo[2,3-c]pyridin-3-yl}ethyl}methylamine;
{2-[1-(2-naphthylsulfonyl)-1H-pyrrolo[2,3-c]pyridin-3-yl]ethyl}methylamine;
{2-[1-(8-quinolinylsulfonyl)-1H-pyrrolo[2,3-c]pyridin-3-yl]-ethyl}methylamine;
{2-{1-[(5-chloro-1,3-dimethyl-1H-pyrazol-4-yl)sulfonyl]-1H-pyrrolo[2,3-c]pyridin-3-yl}ethyl}methylamine;
{2-{1-[(benzo[1,2,5]thiadiazol-4-yl)sulfonyl]-1H-pyrrolo[2,3-c]pyridin-3-yl}ethyl}dimethylamine;
{2-{1-[(7-chlorobenzo[1,2,5]oxadiazol-4-yl)sulfonyl]-1H-pyrrolo[2,3-c]pyridin-3-yl}ethyl}dimethylamine;
{2-{1-[(6-chloroimidazo[2,1-b]thiazol-5-yl)sulfonyl]-1H-pyrrolo[2,3-c]pyridin-3-yl}ethyl}dimethylamine;

{2-{1-[(5-chloro-3-methyl benzo[b]thiophen-2-yl)sulfonyl]-1H-pyrrolo[2,3-c]pyridin-3-yl}ethyl}dimethylamine;
2-{1-[(3-methoxybenzene)sulfonyl]-1H-pyrrolo[2,3-b]pyridin-3-yl}ethylamine;
2-(1-benzenesulfonyl-1H-pyrrolo[2,3-b]pyridin-3-yl)-ethylamine;
2-[(1-benzylsulfonyl)-1H-pyrrolo[2,3-b]pyridin-3-yl]-ethylamine;
2-[1-(2-naphthylsulfonyl)-1H-pyrrolo[2,3-b]pyridin-3-yl]-ethylamine;
2-{1-[(4-methoxybenzene)sulfonyl]-1H-pyrrolo[2,3-b]pyridin-3-yl}ethylamine;
2-{1-[(3,4-dimethoxybenzene)sulfonyl]-1H-pyrrolo[2,3-b]pyridin-3-yl}ethylamine;
2-{1-{[(4-trifluoromethoxy)benzene]sulfonyl}-1H-pyrrolo[2,3-b]pyridin-3-yl}ethylamine;
2-{1-[(2-cyanobenzene)sulfonyl]-1H-pyrrolo[2,3-b]pyridin-3-yl}ethylamine;
2-{1-[(4-cyanobenzene)sulfonyl]-1H-pyrrolo[2,3-b]pyridin-3-yl}ethylamine;
2-{1-{[(2-trifluoromethyl)benzene]sulfonyl}-1H-pyrrolo[2,3-b]pyridin-3-yl}ethylamine;
2-{1-{[(3-trifluoromethyl)benzene]sulfonyl}-1H-pyrrolo[2,3-b]pyridin-3-yl}ethylamine;
2-{1-[(4-t-butylbenzene)sulfonyl]-1H-pyrrolo[2,3-b]pyridin-3-yl}ethylamine;
2-{1-{[(3,5-bis-trifluoromethyl)benzene]sulfonyl}-1H-pyrrolo[2,3-b]pyridin-3-yl}ethylamine;
2-{1-[(4-i-propyl benzene)sulfonyl]-1H-pyrrolo[2,3-b]pyridin-3-yl)ethylamine;
[2-(1-benzenesulfonyl-1H-pyrrolo[2,3-b]pyridin-3-yl)-ethyl]dimethylamine;
[2-(1-benzylsulfonyl-1H-pyrrolo[2,3-b]pyridin-3-yl)-ethyl]dimethylamine;
{2-[1-(2-naphthylsulfonyl)-1H-pyrrolo[2,3-b]pyridin-3-yl]ethyl}dimethylamine;
{2-{[1-(3-methoxybenzene)sulfonyl]-1H-pyrrolo[2,3-b]pyridin-3-yl}ethyl}dimethylamine;
{2-{[1-(4-methoxybenzene)sulfonyl]-1H-pyrrolo[2,3-b]pyridin-3-yl}ethyl}dimethylamine;
{2-{[1-(3,4-dimethoxybenzene)sulfonyl]-1H-pyrrolo[2,3-b]pyridin-3-yl}ethyl}dimethylamine;
{2-{[1-((4-trifluoromethoxy)benzene)sulfonyl]-1H-pyrrolo[2,3-b]pyridin-3-yl}ethyl}dimethylamine;
{2-[1-(2-cyanobenzenesulfonyl)-1H-pyrrolo[2,3-b]pyridin-3-yl]ethyl}dimethylamine;
{2-[1-(4-cyanobenzenesulfonyl)-1H-pyrrolo[2,3-b]pyridin-3-yl]ethyl}dimethylamine;
{2-{[1-(2-trifluoromethyl)benzenesulfonyl]-1H-pyrrolo[2,3-b]pyridin-3-yl}ethyl}dimethylamine;
{2-{[1-(3-trifluoromethyl)benzenesulfonyl]-1H-pyrrolo[2,3-b]pyridin-3-yl}ethyl}dimethylamine;
{2-[1-(4-t-butylbenzenesulfonyl)-1H-pyrrolo[2,3-b]pyridin-3-yl]ethyl}dimethylamine;
{2-{[1-(3,5-bis-trifluoromethyl)benzenesulfonyl]-1H-pyrrolo[2,3-b]pyridin-3-yl}ethyl}dimethylamine;
2-{1-{[(4-trifluoromethyl)benzene]sulfonyl}-1H-pyrrolo[2,3-b]pyridin-3-yl}ethylamine;
2-{1-[(2,5-dimethylbenzene)sulfonyl]-1H-pyrrolo[2,3-b]pyridin-3-yl}ethylamine;
2-{1-[(3-chloro-4-fluorobenzene)sulfony])-1H-pyrrolo[2,3-b]pyridin-3-yl}ethylamine;
2-{1-[(2-chloro-4-fluorobenzene)sulfonyl]-1H-pyrrolo[2,3-b]pyridin-3-yl}ethylamine;
2-{1-[(3-chloro-4-fluorobenzene)sulfonyl]-1H-pyrrolo[2,3-b]pyridin-3-yl}ethylamine;
2-{1-[(3-chloro-2-methylbenzene)sulfonyl]-1H-pyrrolo[2,3-b]pyridin-3-yl}ethylamine;
2-{1-[(3-fluoro-6-methylbenzene)sulfonyl]-1H-pyrrolo[2,3-b]pyridin-3-yl}ethylamine;
2-{1-[(3-chloro-6-methoxybenzene)sulfonyl]-1H-pyrrolo[2,3-b]pyridin-3-yl}ethylamine;
2-{1-[(4-chloro-2,5-dimethylbenzene)sulfonyl]-1H-pyrrolo[2,3-b]pyridin-3-yl}ethylamine;
2-{1-[(2-fluorobenzene)sulfonyl]-1H-pyrrolo[2,3-b]pyridin-3-yl}ethylamine;
2-{1-[(3-fluorobenzene)sulfonyl]-1H-pyrrolo[2,3-b]pyridin-3-yl}ethylamine;
2-{1-[(4-fluorobenzene)sulfonyl]-1H-pyrrolo[2,3-b]pyridin-3-yl}ethylamine;
2-{1-[(2,4-difluorobenzene)sulfonyl]-1H-pyrrolo[2,3-b]pyridin-3-yl}ethylamine;
2-{1-[(3,4-difluorobenzene)sulfonyl]-1H-pyrrolo[2,3-b]pyridin-3-yl}ethylamine;
2-{1-[(2,3,4-trifluorobenzene)sulfonyl]-1H-pyrrolo[2,3-b]pyridin-3-yl}ethylamine;
2-{1-[(2-chlorobenzene)sulfonyl]-1H-pyrrolo[2,3-b]pyridin-3-yl}ethylamine;
2-{1-[(3-chlorobenzene)sulfonyl]-1H-pyrrolo[2,3-b]pyridin-3-yl}ethylamine;
2-{1-[(4-chlorobenzene)sulfonyl]-1H-pyrrolo[2,3-b]pyridin-3-yl}ethylamine;
2-{1-[(2,3-dichlorobenzene)sulfonyl]-1H-pyrrolo[2,3-b]pyridin-3-yl}ethylamine;
2-{1-[(2,5-dichlorobenzene)sulfonyl]-1H-pyrrolo[2,3-b]pyridin-3-yl}ethylamine;
2-{1-[(3,3-dichlorobenzene)sulfonyl]-1H-pyrrolo[2,3-b]pyridin-3-yl}ethylamine;
2-{1-[(2,4-dichlorobenzene)sulfonyl]-1H-pyrrolo[2,3-b]pyridin-3-yl}ethylamine;
2-{1-[(2,4,5-trichlorobenzene)sulfonyl]-1H-pyrrolo[2,3-b]pyridin-3-yl}ethylamine;
2-{1-[(2,4,6-trichlorobenzene)sulfonyl]-1H-pyrrolo[2,3-b]pyridin-3-yl}ethylamine;
2-{1-[(5-chlorothiophen-2-yl)sulfonyl]-1H-pyrrolo[2,3-b]pyridin-3-yl}ethylamine;
2-{1-[(5-bromothiophen-2-yl)sulfonyl]-1H-pyrrolo[2,3-b]pyridin-3-yl}ethylamine;
2-{1-[(4,5-dichlorothiophen-2-yl)sulfonyl]-1H-pyrrolo[2,3-b]pyridin-3-yl}ethylamine;
2-{1-[(2,5-dichlorothiophen-3-yl)sulfonyl]-1H-pyrrolo[2,3-b]pyridin-3-yl}ethylamine;
2-{1-[(4,5-dibromothiophen-2-yl)sulfonyl]-1H-pyrrolo[2,3-b]pyridin-3-yl}ethylamine;
2-{1-[(3-bromo-5-chlorothiophen-2-yl)sulfonyl]-1H-pyrrolo[2,3-b]pyridin-3-yl}ethylamine;
2-{1-[(4-bromo-5-chlorothiophen-2-yl)sulfonyl]-1H-pyrrolo[2,3-b]pyridin-3-yl}ethylamine;
2-{1-[(3-bromo-2,5-dichlorothiophen-4-yl)sulfonyl]-1H-pyrrolo[2,3-b]pyridin-3-yl}ethylamine;
2-{1-[(2-chloroimidazo[1,2-a]pyridin-3-yl)sulfonyl]-pyrrolo[2,3-b]pyridin-3-yl}-ethylamine;
N-{5-[3-(2-aminoethyl)-pyrrolo[2,3-b]pyridine-1-sulfonyl]4-methylthiazol-2-yl}-acetamide;
2-{1-[(1,2-dimethyl-1H-imidazol-4-yl)sulfonyl]-1H-pyrrolo[2,3-b]pyridin-3-yl}ethylamine;
2-{1-[(5-chloro-1,3-dimethyl-1H-pyrazol-4-yl)sulfonyl]-1H-pyrrolo[2,3-b]pyridin-3-yl}ethylamine;
2-{1-[(3,5-dimethylisoxazol-4-yl)sulfonyl]-1H-pyrrolo[2,3-b]pyridin-3-yl}ethylamine;
2-{1-[(benzo[1,2,5]oxadiazole-4-sulfonyl]-1H-pyrrolo[2,3-b]pyridin-3-yl}ethylamine;

2-{1-[(benzo[1,2,5]thiadiazole-4-sulfonyl]-1H-pyrrolo[2,3-b]pyridin-3-yl}ethylamine;
2-{1-[(6-chloroimidazo[2,1-b]thiazol-5-yl)sulfonyl]-1H-pyrrolo[2,3-b]pyridin-3-yl}ethylamine;
2-{1-[(imidazo[2,1-b]thiazol-5-yl)sulfonyl]-1H-pyrrolo[2,3-b]pyridin-3-yl}ethylamine;
2-{1-([3-methylbenzene)sulfonyl]-1H-pyrrolo[2,3-b]pyridin-3-yl}ethylamine;
2-{1-([3-bromobenzene)sulfonyl]-1H-pyrrolo[2,3-b]pyridin-3-yl}ethylamine;
2-{1-[(2,6-dichloroimidazo[2,1-b]thiazol-5-yl)sulfonyl]-1H-pyrrolo[2,3-b]pyridin-3-yl}ethylamine;
{2-{1-[(4-trifluoromethyl)benzenesulfonyl]-1H-pyrrolo[2,3-b]pyridin-3-yl}ethyl}dimethylamine;
{2-{1-[(2-chloro-4-fluorobenzene)sulfonyl]-1H-pyrrolo[2,3-b]pyridin-3-yl}ethyl}dimethylamine;
{2-{1-[(3-chloro-6-methoxybenzene)sulfonyl]-1H-pyrrolo[2,3-b]pyridin-3-yl}ethyl}dimethylamine;
{2-{1-[(4-chloro-2,5-dimethylbenzene)sulfonyl]-1H-pyrrolo[2,3-b]pyridin-3-yl}ethyl}dimethylamine;
{2-{1-[(2-fluorobenzene)sulfonyl]-1H-pyrrolo[2,3-b]pyridin-3-yl}ethyl}dimethylamine;
{2-{1-[(3-fluorobenzene)sulfonyl]-1H-pyrrolo[2,3-b]pyridin-3-yl}ethyl}dimethylamine;
{2-{1-[(3,4-difluorobenzene)sulfonyl]-1H-pyrrolo[2,3-b]pyridin-3-yl}ethyl}dimethylamine;
{2-{1-[(2,3,4-trifluorobenzene)sulfonyl]-1H-pyrrolo[2,3-b]pyridin-3-yl}ethyl}dimethylamine;
{2-{1-[(5-chlorothiophen-2-yl)sulfonyl]-1H-pyrrolo[2,3-b]pyridin-3-yl}ethyl}dimethylamine;
{2-{1-[(2,5-dichlorothiophen-3-yl)sulfonyl]-1H-pyrrolo[2,3-b]pyridin-3-yl}ethyl}dimethylamine;
{2-{1-[(2-Chloroimidazo[1,2-a]pyridin-3-yl)sulfonyl]-1H-pyrrolo[2,3-b]pyridin-3-yl}ethyl}dimethylamine; or the stereoisomers thereof; or the pharmaceutically acceptable salts thereof.

Compounds of the invention may be conveniently prepared using conventional synthetic methods and, if required, standard separation and isolation techniques. For example, compounds of formula I wherein W is $SO_2$ and $R_5$ and $R_6$ are other than H(Ia) may be prepared by reacting an azaindole derivative of formula II with a base such as potassium t-butoxide or sodium hydride followed by a sulfonyl chloride, $R_{10}SO_2Cl$, to give the desired formula Ia product. The reaction sequence is shown in flow diagram I.

FLOW DIAGRAM I

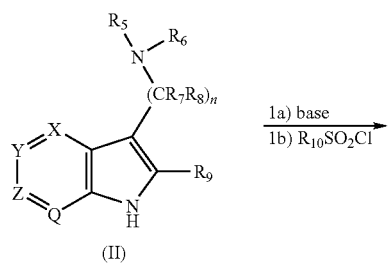

(II)

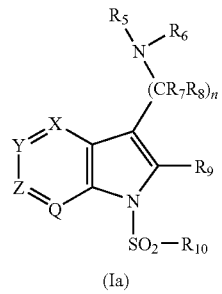

(Ia)

For intermediates of formula II wherein $R_5$ or $R_6$ are H, the formula II amine may be protected with a conventional protecting reagent such as di-t-butyl carbonate, prior to the final sulfonylation steps. The resulting N-protected formula I compound may then be deprotected in the presence of acid.

Similarly, compounds of formula I wherein W is CO, $CONR_{11}$ or $CSNR_{12}$ may be prepared by reacting the formula II substrate and the appropriately substituted acid chloride, isocyanate or isothiocyanate in place of $R_{10}SO_2Cl$.

Protecting groups useful in the reactions described hereinabove include t-butylcarboxylate, benzyl, acetyl, benzyloxycarbonyl, or any conventional group known to protect a basic nitrogen in standard synthetic procedures.

Azaindoles such as 4-azaindole, 5-azaindole, 6-azaindole, or 7-azaindole may be prepared by methods described in the literature, i.e., I. Mahadevan, I., Rasmussen, M., *J. Het. Chem.*, 1992, 29, 359-367; Hands, D.; Bishop, B.; Cameron, M.; Edwards, J. S.; Cottrell, I. F.; Wright, S. H. B., *Synthesis*, 1996, 877-882; Dobson, D.; Todd, A.; Gilmore, J., *Synth. Commun.* 1991, 21, 611-167. In addition, azaindoles are also available commercially, such as 7-azaindole from Aldrich Co.

For example, azaindoles of formula V may be prepared by the reduction of a substituted nitropyridine of formula III to the corresponding aniline via hydrogenation over Raney-Nickel; subsequent conversion to the pivaloyl amide by reaction with pivaloyl chloride in the presence of a base; followed by deprotonation with tert-butyl lithium and entrapment with iodine to give the iodo compound of formula IV. Coupling the formula IV compound with an acetylene in the presence of a palladium catalyst, followed by removal of the trimethylsilyl group with aluminum chloride, gives the substituted azaindole of formula V (D. Mazeas, F. Guillaumet, M-C. Viaud, *Heterocycles* 1999, 50, 1065). The reaction sequence is shown in flow diagram II wherein Et is ethyl, t-Bu is tertiary-butyl, Me is methyl, and Ph is phenyl.

FLOW DIAGRAM II

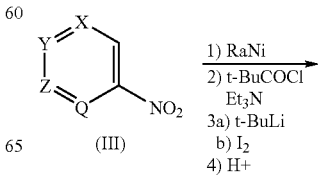

(III)

1) RaNi
2) t-BuCOCl
   $Et_3N$
3a) t-BuLi
   b) $I_2$
4) H+

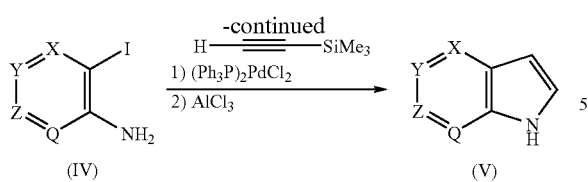

Alternatively, a substituted nitropyridine of formula III is reacted with 4-chlorophenoxyacetonitrile in the presence of potassium tert-butoxide to give the compound of formula VI. Reduction by hydrogenation over palladium on charcoal of the formula VI compound gives the desired azaindole of formula V. (M. Makosza, *Synthesis* 1991, 103). The reaction is shown in flow diagram III.

FLOW DIAGRAM III

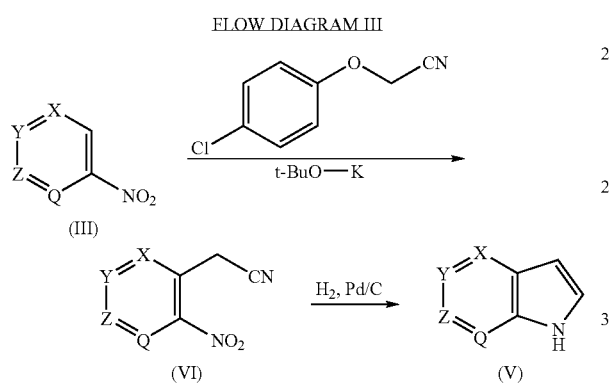

Azaindoles of formula V may also be prepared by the reaction of nitropyridines of formula III with excess vinyl magnesium bromide. (Dobson, D.; Todd, A.; Gilmore, J., *Synth. Commum.* 1991, 21, 611-167). The reaction is shown in flow diagram IV.

FLOW DIAGRAM IV

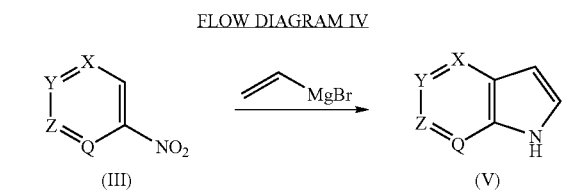

Azaindolylalkylamines of formula XI may be prepared by the reaction of an azaindole with methyl magnesium iodide and zinc chloride, followed by the addition of methyl chlorooxoacetate to give the azaindole glyoxyl methyl ester of formula VIII. (Shadrina, L. P.; Dormidontov, Yu. P.; Ponomarev, V. G.; Lapkin, I. I., *Khim. Geterotsikl. Soedin.,* 1987, 1206-1209). Hydrolysis of the formula VIII methyl ester affords the compound of formula IX which may be coupled with an amine, $HNR_5R_6$, under standard amide bond-forming conditions, for example 3-(diethoxyphosphoryloxy)-1,2,3-benzotriazin-4(3H)-one (DEPBT) in the presence of N,N-diisopropylethylamine (DIEA), to give the amide of formula X which may then be reduced with $LiAlH_4$ to give the desired azaindolylalkyl amine of formula XI.

Compounds of formula X may also be obtained by the reaction of the formula V azaindole with methyl magnesium iodide and zinc chloride followed by oxalyl chloride to give the glyoxyl chloride, which is further reacted with an amine, $HNR_5R_6$, to give the desired formula X amide. Reduction with lithium aluminum hydride gives the desired amine of formula XI. The reactions are shown in flow diagram V.

FLOW DIAGRAM V

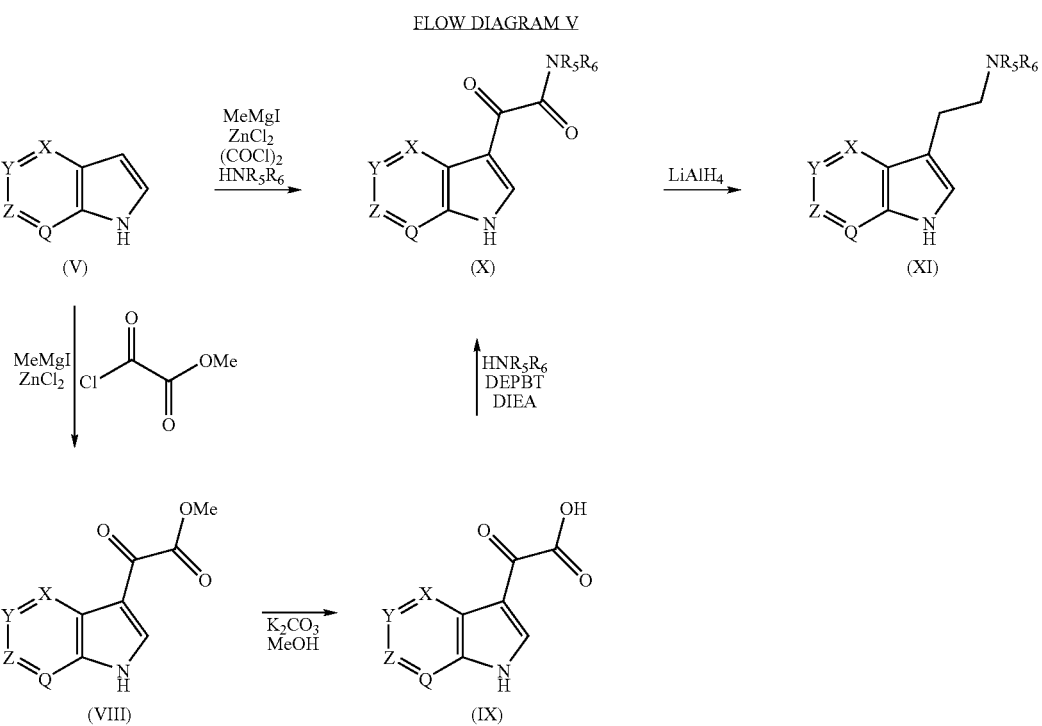

Free amine derivatives of formula XIV may be obtained by the reaction of an azaindole of formula V with dimethylamine and formaldehyde in refluxing butanol to give the formula XII azagramine. Quaternization of the formula XII compound with dimethylsulfate followed by reaction with potassium cyanide affords the nitrile of formula XIII. Said nitrile may be reduced to the desired free amine of formula XI with Adams catalyst and hydrochloric acid in ethanol or with Raney-Nickel in methanolic ammonia. The reaction is shown in flow diagram VI.

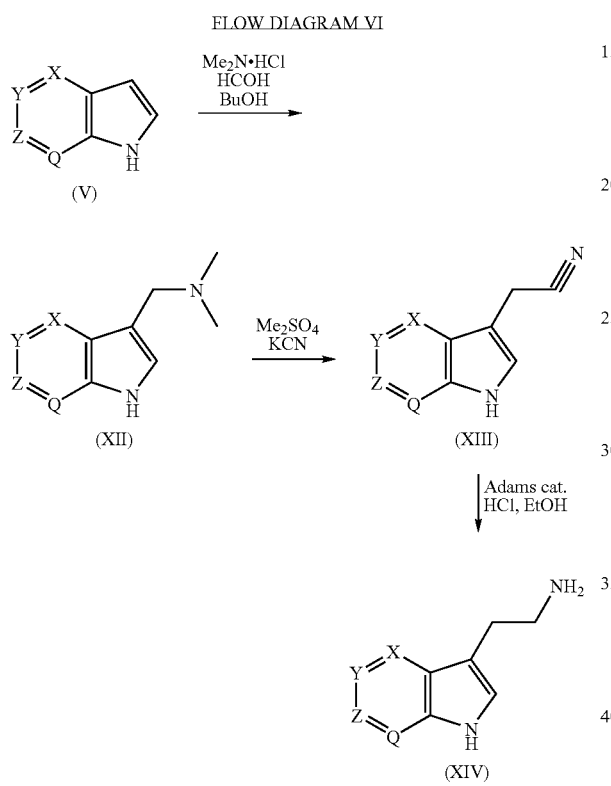

Branched alkylamines of formula XVII may be prepared by reacting a formula V azaindole with Vilsmeier reagent to give the 3-formylazaindole of formula XV. Said 3-formylazaindoles are reacted with a nitroalkane, $R_8CH_2NO_2$, in the presence of ammonium acetate to give a compound of formula XVI. Reduction of the formula XVI compound with sodium borohydride, followed by hydrogenation over Raney-Nickel gives the desired branched alkylamine of formula XVII. (M-C. Viaud, A. Mamai, V. Guerin, C. Bennejean, P. Renard, P. Delagrange, B. Guardiola-Lemaitre, H. E. Howell, G. Guillaumet, *Pharm. Pharmacol. Commum.*, 1998, 4, 47). The reaction is shown in flow diagram VII.

FLOW DIAGRAM VII

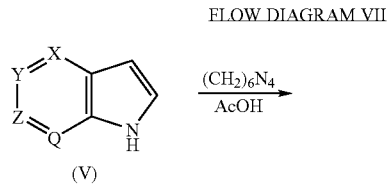

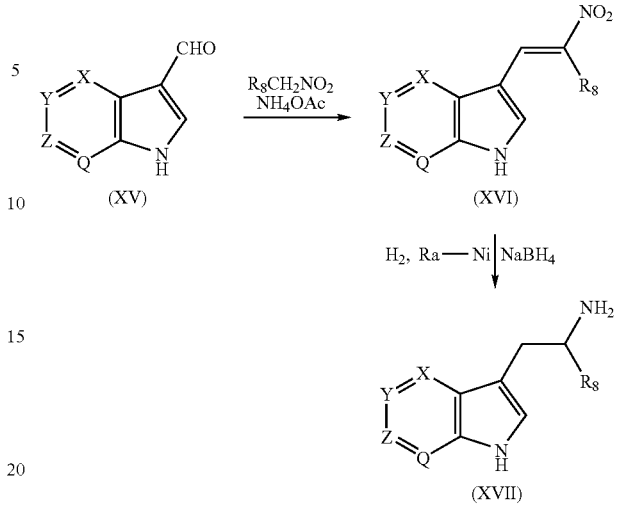

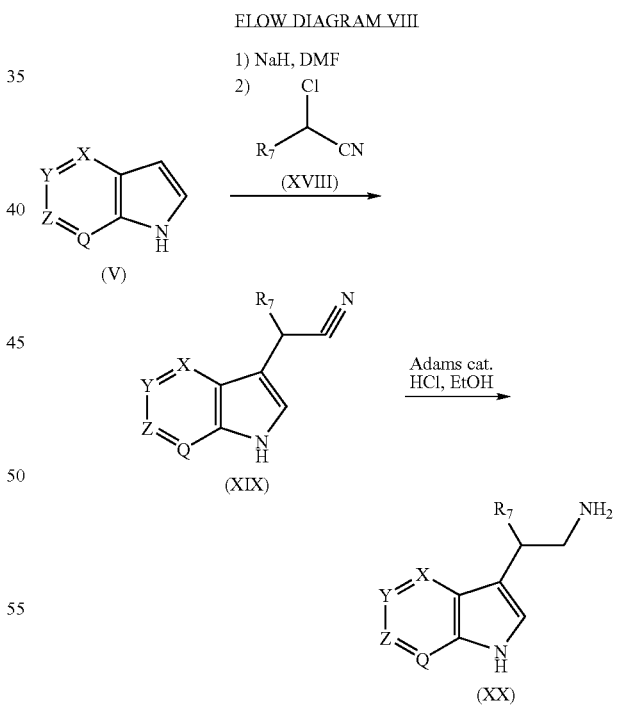

Branched alkylamines may also be prepared by the reaction of a formula V azaindole with sodium hydride in DMF followed by the addition of a chloroacetonitrile of formula XVIII to form the compound of formula XIX. The formula XIX compound may then be reduced with Adams catalyst as described above to give the desired formula XX compound. The reaction is shown in flow diagram VIII.

Branched alkylamine derivatives of formula XXIII may also be obtained directly from the iodoaminopyridine of formula XXI by the palladium catalyzed coupling of said pyridine with a suitable acetylene to give the azaindole of formula XXII. Reaction of the formula XXII compound with $AlCl_3$ gives the desired product of formula XXIII. The reaction is shown in flow diagram IX.

FLOW DIAGRAM IX

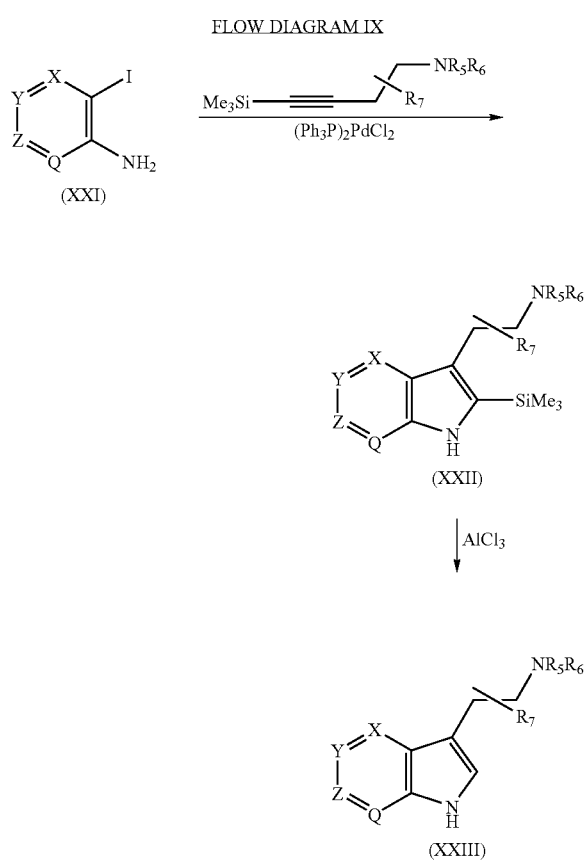

Sulfonyl chlorides, $R_{10}SO_2Cl$, may be obtained commercially or prepared by conventional techniques. For example, 6-substituted-imidazo[2,1-b][1,3]thiazol-5-yl sulfonyl chlorides of formulas XXVIa and XXVIb may be prepared by reacting 2-amino thiazole with chloroacetic acid or a suitable chloromethyl ketone to give 2-imino-4-thiazolin-3-ylacetic acid (XXIVa) or the 2-imino-4-thiazolin-3-yl ketone (XXIVb), respectively; reacting either XXIVa or XXIVb with $POCl_3$ to give, in the case of XXIVa, 6-chloroimidazo[2,1-b]thiazole (XXVa) or, in the case of XXIVb, 6-substituted-imidazo[2,1-b]thiazole XXVb; and sequentially reacting the respective XXVa and XXVb compounds with chlorosulfonic acid and $POCl_3$ to give the desired sulfonyl chlorides of formulas XXVIa and XXVIb. The reactions are illustrated in flow diagram X wherein R represents an optional substituent as described hereinabove with the exclusion of halogen.

FLOW DIAGRAM X

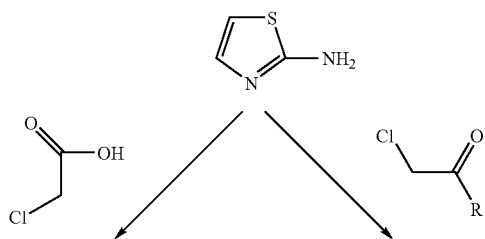

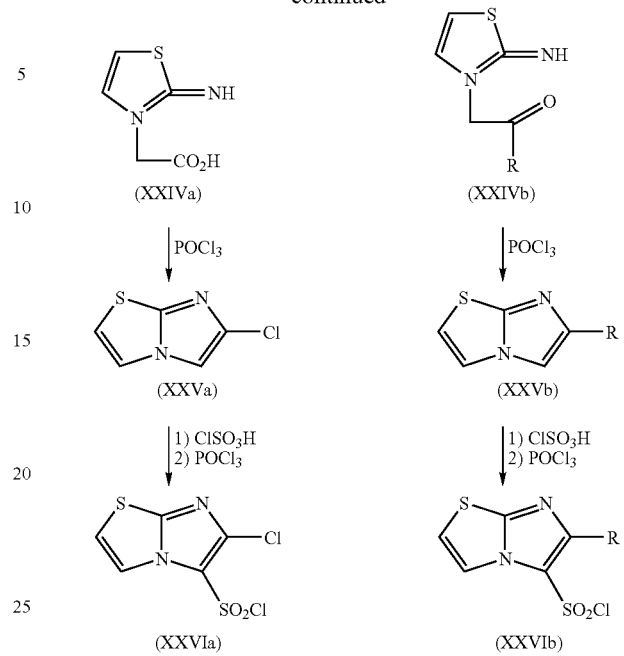

In addition to the procedures described hereinabove in flow diagrams I through X, the compounds of the invention may be prepared according to the procedures described in the Examples set forth hereinbelow.

Advantageously, the present invention provides a method for the preparation of a compound of formula I wherein W is $SO_2$ and $R_5$ and $R_6$ are other than H (Ib) which comprises reacting a compound of formula II with a sulfonyl chloride, $R_{10}SO_2Cl$, in the presence of a base optionally in the presence of a solvent. The process is shown in flow diagram XI.

FLOW DIAGRAM XI

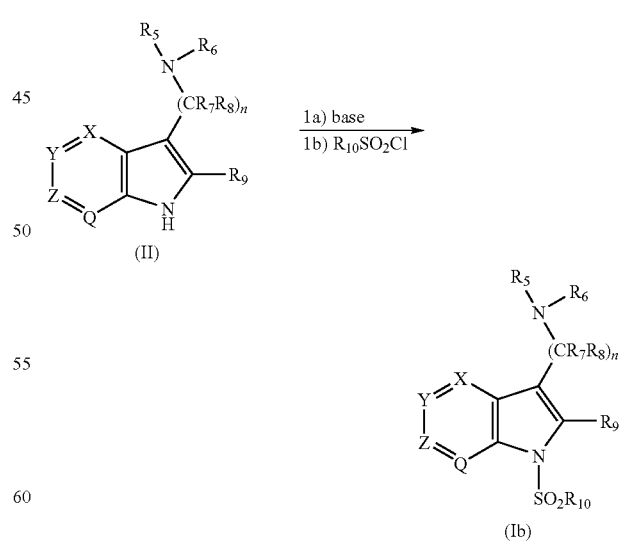

Bases suitable for use in the method of invention are strong bases such as NaH, KOt-Bu, or any conventional base capable of removing a proton from a basic indole or benzazole nitrogen atom.

Advantageously, the inventive compound of formula I may be utilized in the treatment of central nervous system disorders relating to or affected by the 5-HT6 receptor such as motor, mood, psychiatric, cognitive, neurodegenerative, or the like disorders, for example, Alzheimer's disease, Parkinson's disease, attention deficit disorder, anxiety, epilepsy, depression, obsessive compulsive disorder, migraine, sleep disorders, neurodegenerative disorders (such as head trauma or stroke), feeding disorders (such as anorexia or bulimia), schizophrenia, memory loss, disorders associated with drawl from drug or nicotine abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms NMR and HPLC designate nuclear magnetic resonance and high performance liquid chromatography, respectively. The terms THF and EtOAc designate tetrahydrofuran and ethyl acetate, respectively. The terms TFA and DMF designate trifluoroacetic acid and dimethyl formamide, respectively.

EXAMPLE 1

Preparation of 2-[1-(2-Chlorobenzenesulfonyl)-1H-pyrrolo[3,2-b]pyridin-3-yl]ethylamine

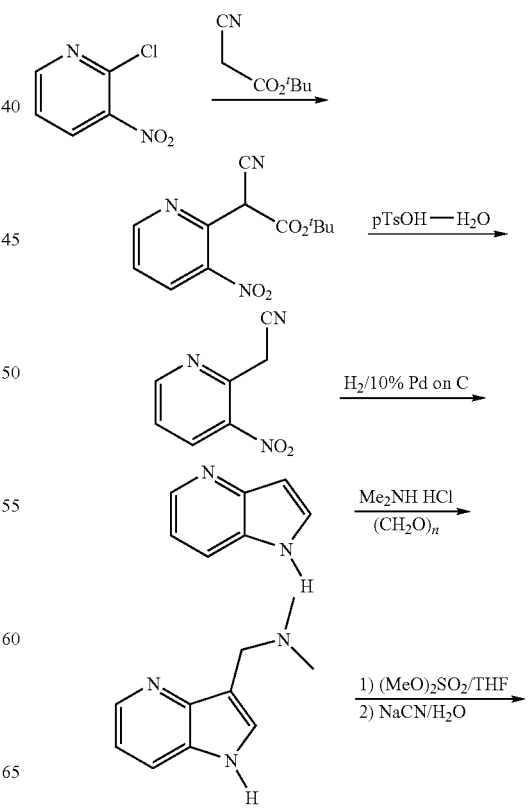

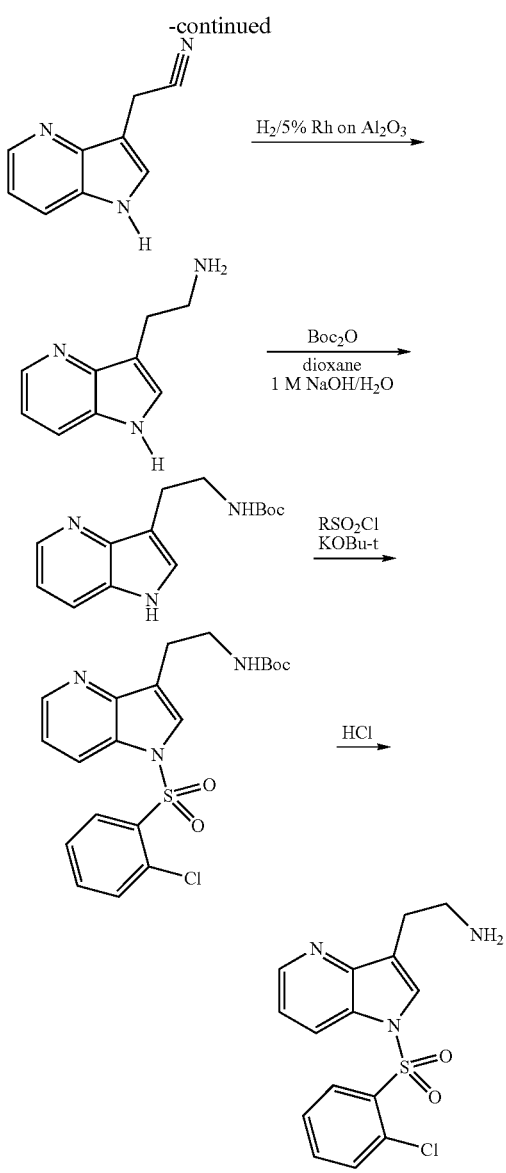

Steps 1 & 2. Preparation of (3-NITROPYRIDIN-2-YL)ACETO-NITRILE

Using the procedure of R. B. Katz, M. Voyle, *Synthesis*, 314-316 (1989), a mixture of 2-chloro-3-nitro-pyridine (9.51 g, 60 mmol), $K_2CO_3$ (20.7 g, 150 mmol) and t-butyl cyanoacetate (13.0 mL, 90 mmol) in THF is heated at reflux temperature for 24 h, cooled and concentrated in vacuo. The residue is suspended in 1:1 water/$CH_2Cl_2$ and carefully acidified to pH 1 with concentrated hydrochloric acid. The layers are separated and the organic layer is dried over $MgSO_4$ and concentrated in vacuo to a dark oil. This oil is treated with p-toluene-sulfonic acid monohydrate (1.0 g) and toluene, heated at reflux temperature for 2 h, cooled and decanted. The dark residue is washed with $CH_2Cl_2$. The combined $CH_2Cl_2$ washes and toluene superinnate are washed with saturated aqueous $NaHCO_3$, dried over $MgSO_4$ and concentrated in vacuo to an oily solid. Trituration with 20:80 ethyl acetate: hexanes gives the title compound as an orange-brown solid, 6.50 g, (66% yield), mp 106-108° C., identified by NMR and mass spectral analyses.

Step 3. Preparation of 4-AZAINDOLE

A mixture of (3-nitropyridin-2-yl)acetonitrile (4.89 g, 30.0 mmol) and 10% palladium on carbon (0.50 g) in ethanol (100 mL) and glacial acetic acid (6.0 mL) is hydrogenated under 55 psi of hydrogen in a Parr apparatus for 24 h. The reaction is filtered through Celite and concentrated in vacuo to a green oil which is treated with water (25 mL) and $NaHCO_3$ (~10 g). The resulting mixture is extracted with $CH_2Cl_2$. The combined extracts are dried over $MgSO_4$ and concentrated in vacuo. Chromatography (silica gel, ethyl acetate) of the resultant residue affords the title azaindole compound as a pale pink solid, 2.40 g (68% yield), mp 126-128° C., identified by NMR and mass spectral analyses.

Step 4. Preparation of N,N-DIMETHYL-(1H-PYRROLO[3,2-B]PYRIDIN-3-YL)METHYLAMINE A solution of 4-azaindole (0.880 g, 7.45 mmol), dimethylamine hydrochloride (0.67 g, 8.19 mmol) and paraformaldehyde (0.25 g, 8.19 mmol eq.) in 1-butanol is heated at reflux temperature for 3 h, cooled, concentrated in vacuo, treated with water and saturated aqueous $NaHCO_3$ and extracted with 4:1 $CH_2Cl_2$:ethanol. The combined extracts are dried over $MgSO_4$ and concentrated in vacuo. The resultant residue is chromatographed (silica gel, ethyl acetate, followed by 5:95 triethylamine:ethanol as eluent) to afford the title compound as a tan solid, 0.838 g (64% yield), identified by NMR analysis.

Step 5. Preparation of (1H-PYRROLO[3,2-B]PYRIDIN-3-YL)-ACETONITRILE

A stirred solution of dimethyl-(1H-pyrrolo[3,2-b]pyridin-3-yl)methylamine (0.828 g, 4.73 mmol) in dry THF (20 mL) under nitrogen is treated with a solution of $(CH_3O)_2SO_2$ (0.49 mL) in THF, heated at reflux temperature for 0.5 h, cooled in an ice bath, and decanted. The gummy residue is washed with ether, treated with water (15 mL) and NaCN (0.39 g, 6.2 mmol), heated at reflux temperature for 0.75 h, cooled and extracted with 4:1 $CH_2Cl_2$:ethanol. The combined extracts are dried over $MgSO_4$ and concentrated in vacuo. The resultant residue is chromatographed (silica gel, ethyl acetate as eluent) to afford the title compound as a white solid, 0.51 g (68% yield), mp 201-202° C., identified by NMR and mass spectral analyses.

Steps 6 & 7. Preparation of T-BUTYL [2-(1H-PYRROLO-[3,2-B]PYRIDIN-3-YL)ETHYL] CARBAMATE A mixture of (1H-pyrrolo[3,2-b]pyridin-3-yl)-acetonitrile (1.03 g, 6.55 mmol) and 5% rhodium on alumina (1.03 g) in ethanol (40 mL) and concentrated $NH_4OH$ (20 mL) is placed under 55 psi hydrogen pressure on a Parr shaker. After 24 h at ambient temperature, the reaction is filtered through Celite and concentrated in vacuo. The resultant residue is chromatographed (silica gel, 1:9 conc. NH$_4$OH:ethanol as eluent) to afford the primary amine as a white solid, 1.03 g, 6.39 mmol (98% yield). This solid is dissolved in dioxane and treated with di-t-butyloxydicarbonate (1.39 g, 7.03 mmol) and 1.0 M aqueous NaOH (7.0 mL, 7.0 mmol). After 16 h at ambient temperature, the reaction is treated with water and extracted with CH$_2$Cl$_2$. The combined extracts are dried over MgSO$_4$ and concentrated in vacuo. This residue is chromatographed (silica gel, ethyl acetate as eluent) to afford the title carbamate compound as a white solid, 1.29 g (77% yield), identified by NMR analysis.

Step 8. Preparation of T-BUTYL {2-{1-[(2-CHLORO-BENZENE)SULFONYL]-1H-PYRROLO[3,2-B]PYRIDIN-3-YL}ETHYL}CARBAMATE A solution of t-butyl [2-(1H-pyrrolo[3,2-b]pyridin-3-yl) ethyl]carbamate (26 mg, 1.1 eq.) and 2-chloro-benzenesulfonyl chloride (23 mg, 1.0 eq) in THF at room temperature, is treated with potassium t-butoxide (0.12 mL, 1.0 M solution in THF, 1.2 eq), stirred at room temperature for 16 h and concentrated in vacuo. The resultant residue is used as is in step 9, below.

Step 9. 2-{1-[(2-CHLOROBENZENE)SULFONYL]-1H-PYRROLO[3,2-B]PYRIDIN-3-YL}ETHYLAMINE A solution of t-butyl {2-{1-[(2-chlorobenzene)-sulfonyl]-1H-pyrrolo[3,2-b]pyridin-3-yl}ethyl}carbamate in THF (1 mL) and HCl (4 N in methanol, 1 mL) is stirred for 2 h and concentrated in vacuo. The resultant residue is purified by preparative reverse phase liquid chromatography (HPLC[1]) to give the title product as a white solid, M+H 336; 1.94 min.

[1] Gilson Preparative HPLC conditions: Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLE 2

Preparation of 2-{1-[(2,4-difluorophenyl)sulfonyl]-1H-pyrrolo-[3,2b]pyridin-3-yl}-ethylamine

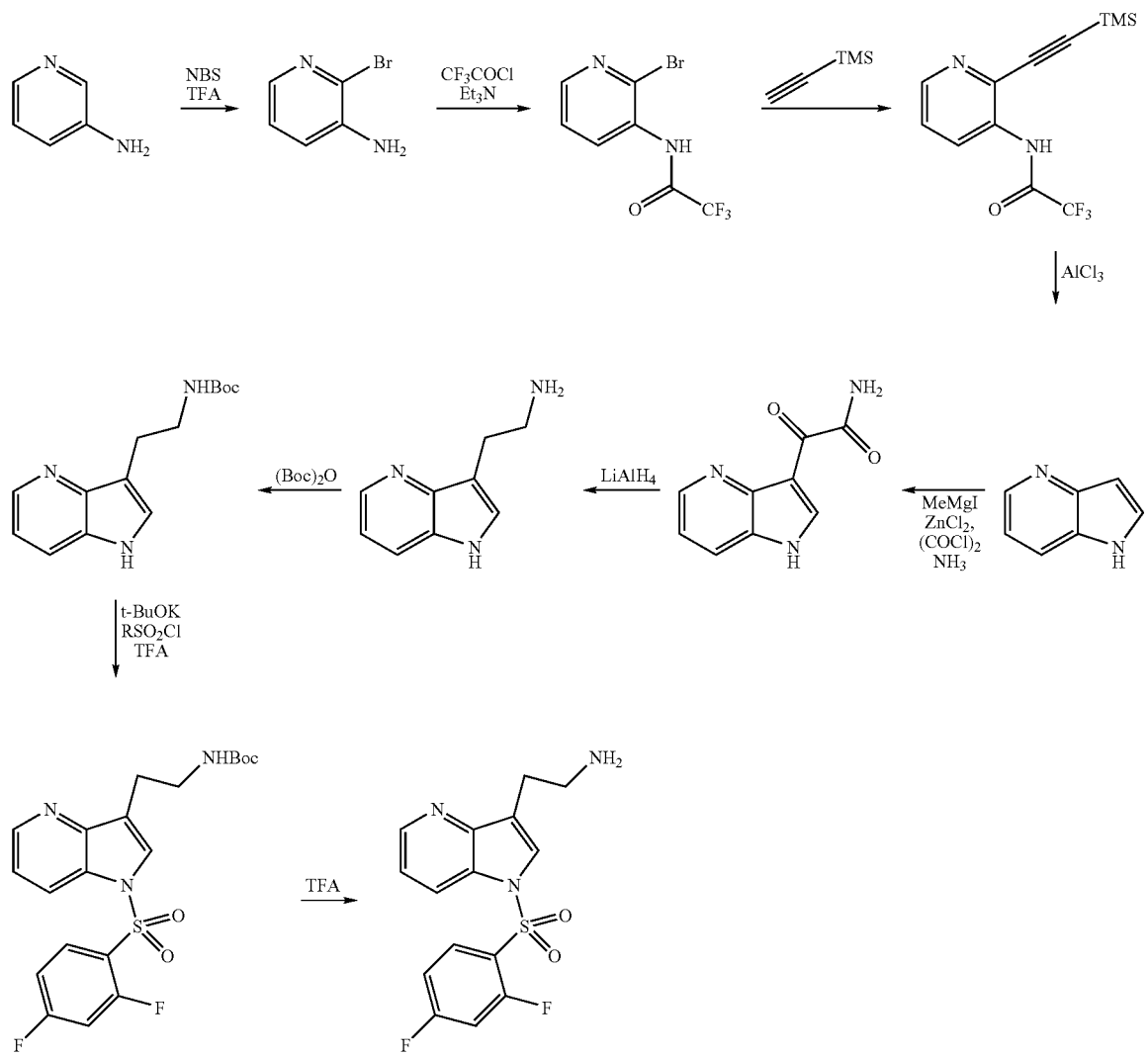

Step 1. Preparation of 3-AMINO-2-BROMOPYRIDINE

A solution of 3-aminopyridine in TFA is treated cautiously with N-bromo-succinimide (NBS) (1.1 eq), stirred for 8 h and concentrated in vacuo. The residue is recrystallized from hexane to afford the title compound.

Step 2. Preparation of 2-BROMO-3-TRIFLUOROACET-AMINOPYRIDINE

A solution of 3-amino-2-bromopyridine in ether at 0° C. is treated with trifluoroacetic anhydride (1.2 eq.) followed by sodium carbonate (1.3 eq), stirred at room temperature for 10 h, then poured into water and extracted with EtOAc. The combined extracts are dried over $MgSO_4$ and concentrated in vacuo. Purification of the resultant residue by silica gel chromatography gives the title compound.

Step 3. Preparation of 2,2,2-TRIFLUORO-N-(2-TRIMETHYLSILANYLETHYNYL-PYRIDIN-3-YL)-ACETAMIDE A mixture of 2-bromo-3-trifluoroacetaminopyridine (1.0 eq.), trimethylsilylacetylene (1.8 eq.), $PdCl_2(PPh_3)_2$ (0.05 eq.), CuI (0.1 eq.) and triethylamine (3.5 eq.) is heated to 100° C. in a sealed tube for 10 h. The solvent is removed under vacuum, and the residue is partitioned between EtOAc and water. The organic phase is dried over $MgSO_4$ and concentrated to give the title compound, which is used without further purification.

Step 4. Preparation of 4-AZAINDOLE

A mixture of 2,2,2-trifluoro-N-(2-trimethylsilan-ylethynylpyridin-3-yl)acetamide (1.0 eq) and sodium ethoxide (5 eq.) in ethanol is heated at reflux temperature for 10 h, cooled and concentrated in vacuo. The resultant residue is purified by preparative reverse phase HPLC to give the title 4-azaindole.

Step 5. Preparation of 2-OXO-2-(1H-PYRROLO[3,2-B]PYRIDIN-3-YL)ACETAMIDE

A solution of 4-azaindole (1.0 eq.) in ether is treated with methyl magnesium iodide (1.1 eq.) at room temperature, stirred for 1 h, treated with zinc chloride (1.2 eq.), stirred for a further 1 h, treated with oxalyl chloride (10 eq.), stirred for 10 h and concentrated in vacuo to give a residue. The residue is dissolved in acetonitrile and pyridine (1.6 eq.), treated with ammonia (2 eq., solution in dioxane), stirred for 1 h and concentrated in vacuo. The concentrate is purified by chromatography [silica gel, $CH_2Cl_2$/methanol (containing 5% ammonium hydroxide) as eluent] to afford the title acetamide compound.

Step 6. 4-AZATRYPTAMINE

A solution of 2-oxo-2-(1H-pyrrolo[3,2-b]pyridin-3-yl)acetamide (1 eq.) in ether is treated with lithium aluminum hydride (4 eq.), heated at reflux temperature for 8 h, cooled to 0° C., quenched by addition of Rochelle's salt solution and extracted with $CH_2Cl_2$. The extracts are combined, dried over $MgSO_4$ and concentrated to afford the title amine, which is used directly in the next step.

Step 7. N-T-BUTYLOXYCARBONYL 4-AZATRYPTAMINE (BOC-4-AZATRYPTAMINE)

A solution of 4-azatryptamine (1.0 eq.) in 1:1 acetone/water is treated with di-t-butyl dicarbonate (1.1 eq.) and potassium carbonate (1.2 eq.), stirred at room temperature for 16 h and concentrated to remove the acetone. The concentrate is extracted with EtOAc; the extracts are combined, dried over $MgSO_4$ and concentrated in vacuo to give a residue. This residue is crystallized from EtOAc/hexane to afford the title protected amine.

Step 8. Preparation of T-BUTYL {2-{1-[(2,4-DIFLUORO-PHENYL)SULFONYL]-1H-PYRROLO[3,2-B]PYRIDIN-3-YL}ETHYL}-CARBAMATE A mixture of Boc-4-azatryptamine (1.1 eq.) and 2,4-difluorobenzenesulfonyl chloride (1.0 eq.) in THF at room temperature is treated portionwise with solid potassium t-butoxide (1.2 eq), stirred at room temperature for 16 h, poured into saturated $NaHCO_3$ and extracted with EtOAc. The combined extracts are dried over $MgSO_4$ and concentrated in vacuo to give a residue. Purification of this residue by chromatography (silica gel, EtOAc/hexanes as eluent) affords the title carbamate compound.

Step 9. Preparation of 2-{1-[(2,4-DIFLUOROPHENYL)-SULFONYL]-1H-PYRROLO-[3,2B]PYRIDIN-3-YL}ETHYLAMINE A solution of t-butyl {2-{1-[(2,4-difluoro-phenyl)sulfonyl]-1H-pyrrolo[3,2-b]pyridin-3-yl}ethyl}-carbamate in methylene chloride is treated with TFA, stirred for 2 h and concentrated in vacuo. The resultant residue is purified by preparative reverse phase HPLC to afford the title product.

EXAMPLES 3-34

2-[1-(Substituted-sulfonyl)-1H-pyrrolo[3,2-b]pyridin-3-yl]-ethylamine derivatives Using essentially the same procedures described for Examples 1 and 2, and utilizing the appropriate amine in step 5 of Example 2 and the appropriate sulfonyl chloride in step 8 of Examples 1 or 2, the compounds shown in Table I are prepared and purified by preparative reverse phase HPLC using the following HPLC conditions: HP 1100 HPLC system; Waters Xterra MS C18, 2 mm (i.d.)×50 mm (length), 3.5 μm column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min % B; Sample concentration: ~2.0 mM; Injection volume: 5 uL; Detection: 220 nm, 254 nm DAD.

TABLE I

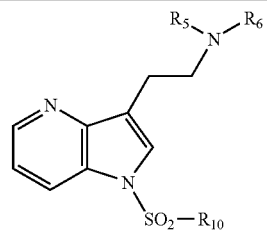

| Ex No | $R_5$ | $R_6$ | $R_{10}$ | M + H | HPLC Min |
|---|---|---|---|---|---|
| 3 | H | H | 1-methyl-1H-imidazol-4-yl | — | — |
| 4 | H | H | 3,5-dimethyl-isoxazol-4-yl | — | — |
| 5 | H | H | 5-chlorothiophene-2-yl | 342 | 2.06 |
| 6 | H | H | naphth-2-yl | 352 | 2.19 |
| 7 | H | H | quinolin-8-yl | — | — |
| 8 | H | H | 5-chloro-1,3-dimethyl-1H-pyrazol-4-yl | — | — |

TABLE I-continued

[Structure with R5, R6, N, and SO2-R10 substituents on pyrrolopyridine]

| Ex No | R5 | R6 | R10 | M + H | HPLC Min |
|---|---|---|---|---|---|
| 9 | H | H | benzo[1,2,5]thiadiazol-4-yl | — | — |
| 10 | H | H | 7-chlorobenzo[1,2,5]oxadia-zol-4-yl | — | — |
| 11 | H | H | 6-chloroimidazo[2,1-b]thiazol-5-yl | 382 | 2.37 |
| 12 | H | H | 5-chloro-3-methylbenzo[b]thio-phen-2-yl | — | — |
| 13 | H | H | 3-(trifluoromethyl)phenyl | 370 | 2.10 |
| 14 | H | H | 2-chloro-4-(trifluoromethyl)-phenyl | 404 | 2.18 |
| 15 | H | H | 3,4-difluorophenyl | 338 | 1.96 |
| 16 | H | H | 3-chlorophenyl | 336 | 2.04 |
| 17 | H | H | 3-methoxyphenyl | 332 | 2.42 |
| 18 | H | H | imidazo[2,1-b]thiazol-5-yl | 348 | 2.17 |
| 19 | H | H | phenyl | 302 | 2.32 |
| 20 | H | H | 3-fluorophenyl | 320 | 2.38 |
| 21 | H | H | 4-aminophenyl | 318 | 2.16 |
| 22 | H | H | 3-methylphenyl | 316 | 2.45 |
| 23 | H | H | 2,3-dichlorophenyl | 371 | 2.55 |
| 24 | H | H | 2-fluorophenyl | 320 | 2.33 |
| 25 | H | H | 3-bromophenyl | 381 | 2.53 |
| 26 | H | H | 2,6-dichloroimidazo[2,1-b]thiazol-5-yl | 417 | 2.55 |
| 27 | H | CH3 | 5-chlorothiophen-2-yl | — | — |
| 28 | H | CH3 | naphth-2-yl | — | — |
| 29 | H | CH3 | quinolin-8-yl | — | — |
| 30 | H | CH3 | 5-chloro-1,3-dimethyl-1H-pyrazol-4-yl | — | — |
| 31 | CH3 | CH3 | benzo[1,2,5]thiadiazol-4-yl | — | — |
| 32 | CH3 | CH3 | 7-chlorobenzo[1,2,5]oxadiazol-4-yl | — | — |
| 33 | CH3 | CH3 | 6-chloroimidazo[2,1-b]thiazol-5-yl | — | — |
| 34 | CH3 | CH3 | 5-chloro-3-methyl-benzo[b]thiophene-2-yl | — | — |

EXAMPLE 35

Preparation of 2-{[1-(6-Chloroimidazo[2,1-b]thiazol-5-yl)sulfonyl]-1H-pyrrolo[3,2-c]pyridin-3-yl}ethylamine

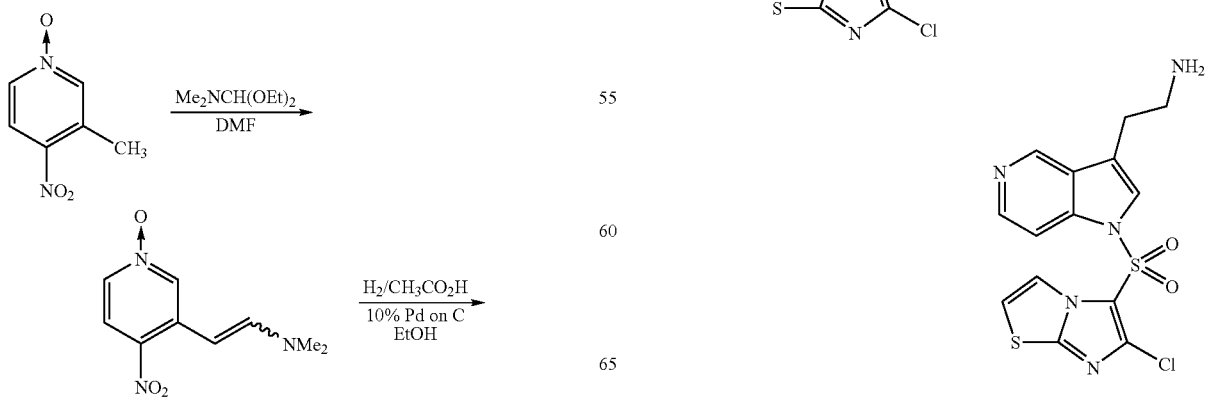

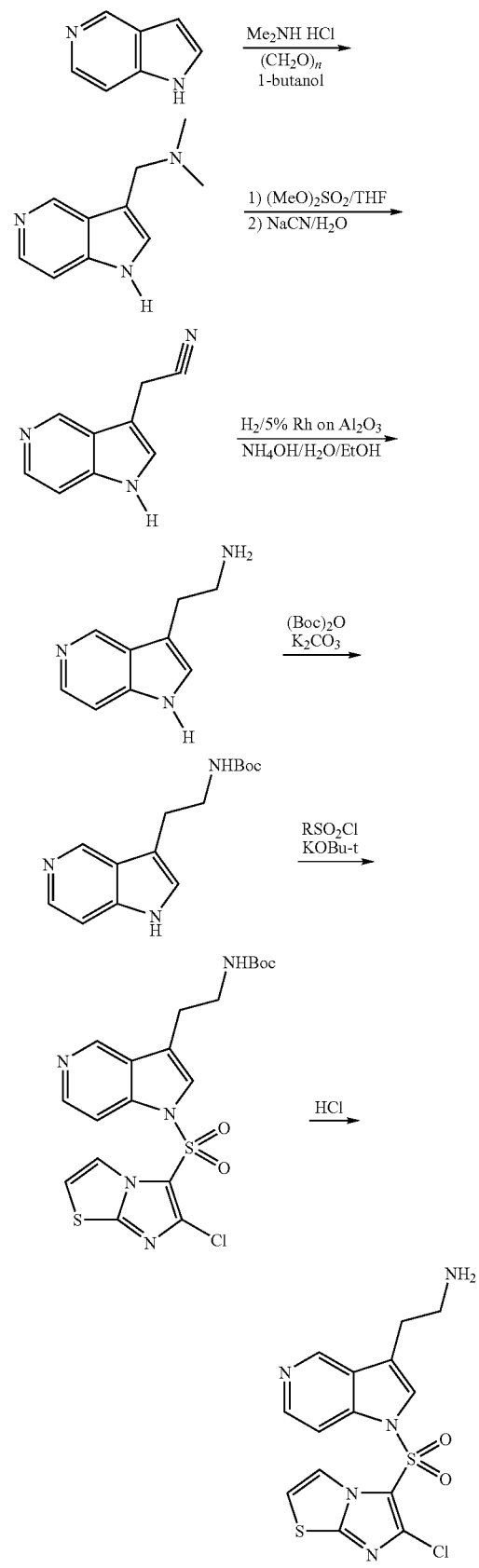

Steps 1 & 2. Preparation of 5-AZAINDOLE

This compound is prepared in a procedure similar to that described by J. R. Dormoy and A. Heymes in *Tetrahedron*, 1993, 49(14), 2885-2914. A stirred solution of 3-methyl-4-nitropyridine N-oxide (10.0 g, 65.0 mmol) and N,N-dimethylformamide diethyl acetal (14.5 g, 99 mmol) in DMF is placed in a preheated bath (90° C.) for 1.25 h, cooled and filtered. The filtercake is rinsed with a small amount of methanol and air-dried to give a purple-brown solid, 12.1 g. A portion of this solid (2.09 g, 10.0 mmol) is dissolved in ethanol (50 mL) and acetic acid (2 mL), treated with 10% palladium on carbon placed under 54 psi of hydrogen on a Parr shaker for 16 h and filtered through Celite. The filtrate is concentrated in vacuo and the concentrate is chromatographed (silica gel, 20:80 ethanol:EtOAc), followed by 50:50 ethanol:EtOAc as eluent) to afford the title 5-azaindole compound as a pink solid, 0.601 g (51% yield), identified by comparison of the NMR to literature (*Can. J. Chem.*, 1969, 47, 3257).

Step 3. Preparation of N,N-DIMETHYL-(1H-PYRROLO[3,2-C]-PYRIDIN-3-YL)METHYLAMINE A solution of 5-azaindole (1.19 g, 10.0 mmol), dimethylamine hydrochloride (0.98 g, 12.0 mmol) and paraformaldehyde (0.36 g, 12.0 mmol-equivalents) in 1-butanol is heated at reflux temperature for 5 h and concentrated in vacuo. The concentrate is diluted with saturated aqueous $NaHCO_3$ and extracted with 4:1 $CH_2Cl_2$:ethanol. The combined extracts are dried over $MgSO_4$, concentrated in vacuo and filtered. The filtercake is air-dried to afford the title compound as a yellow solid, 0.680 g (39% yield), identified by NMR analysis.

Step 4. Preparation of (1H-PYRROLO[3,2-C]PYRIDIN-3-YL)-ACETONITRILE

Using essentially the same procedure described in Example 1, Step 5, hereinabove and employing N,N-dimethyl-(1H-pyrrolo[3,2-c]pyridin-3-yl)methylamine as substrate and 1:2 ethanol:ethyl acetate as the chromatography eluent affords the title acetonitrile as a yellow solid, 0.160 g (26% yield), identified by NMR analysis.

Step 5. Preparation of 5-AZATRYPTAMINE

A mixture of (1H-pyrrolo[3,2-c]pyridin-3-yl)-acetonitrile (0.260 g, 1.66 mmol) and 5% rhodium on alumina (0.26 g) in ethanol (10 mL) and concentrated $NH_4OH$ (5 mL) is placed under 55 psi hydrogen pressure on a Parr shaker. After 24 h at ambient temperature, the reaction mixture is filtered through Celite and concentrated in vacuo to afford the title amine, identified by NMR and mass spectral analyses.

Step 6. Preparation of T-BUTYL 3-[(2-T-BUTOXYCARBONYL)AMINOETHYL]PYRROLO[3,2-C]PYRIDINE-1-CARBOXYLATE (BOC-5-AZATRYPTAMINE)

A solution of 5-azatryptamine (107 mg) in 1:1 acetone/water is treated with di-t-butyl dicarbonate (146 mg, 1.1 eq.) and potassium carbonate (184 mg, 2 eq.), stirred at room temperature for 16 h, concentrated in vacuo to remove the acetone and extracted with EtOAc. The extracts are combined, dried over $MgSO_4$ and concentrated in vacuo to afford the title protected amine, identified by HPLC and mass spectral analyses.

Step 7. Preparation of T-BUTYL {2-{[1-(6-CHLOROIMIDAZO[2,1-B]THIAZOLE-5-YL)SULFONYL]-1H-PYRROLO[3,2-C]PYRIDIN-3-YL}ETHYL}-CARBAMATE A solution of Boc-5-azatryptamine (26 mg, 1.1 eq.) and (6-chloroimidazo[2,1-b]thiazol-5-yl)sulfonyl chloride (23 mg, 1.0 eq.) in THF is treated with potassium t-butoxide (0.12 mL, 1.0 M solution in THF, 1.2 eq), stirred at room temperature for 16 h and concentrated in vacuo to afford the title compound, identified by NMR analysis.

Step 8. Preparation of 2-{[1-(6-CHLORO-IMIDAZO[2,1-B]THIAZOL-5-YL)SULFONYL]-1H-PYRROLO[3,2-C]PYRIDIN-3-YL}-ETHYLAMINE A solution of t-butyl {2-{[1-(6-chloroimidazo[2,1-b]thiazole-5-yl)sulfonyl]-1H-pyrrolo[3,2-c]pyridin-3-yl}ethyl}-carbamate in THF, is treated with HCl (4 N in methanol) stirred for 2 h and concentrated in vacuo. The resultant residue is purified by preparative reverse phase HPLC[1], M+H 382, 1.93 min.

[1]Gilson Preparative HPLC conditions: Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; min: 10% A, 15 min: 10% A, 16 min: 95% A; Flow rate 22.5 mL/min; Detection: 254 nm DAD.

EXAMPLE 36

Preparation of 2-{1-[(2,4-Difluorophenyl)sulfonyl]-1H-pyrrolo[3,2-c]pyridin-3-yl}ethylamine

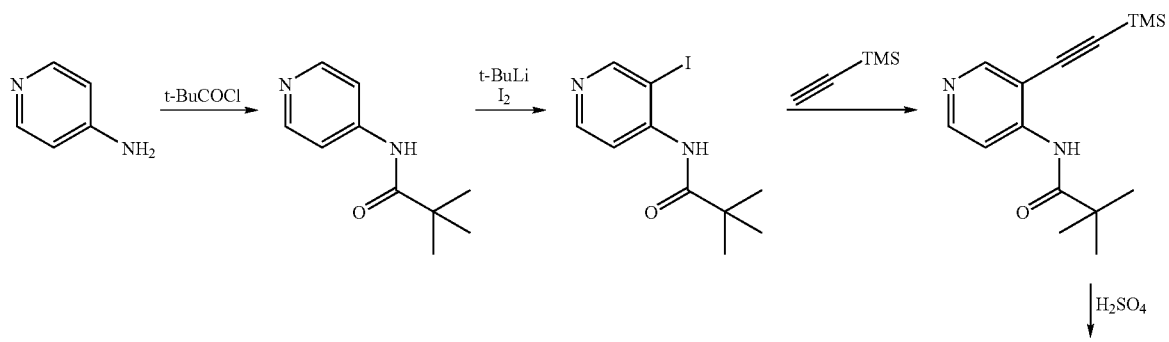

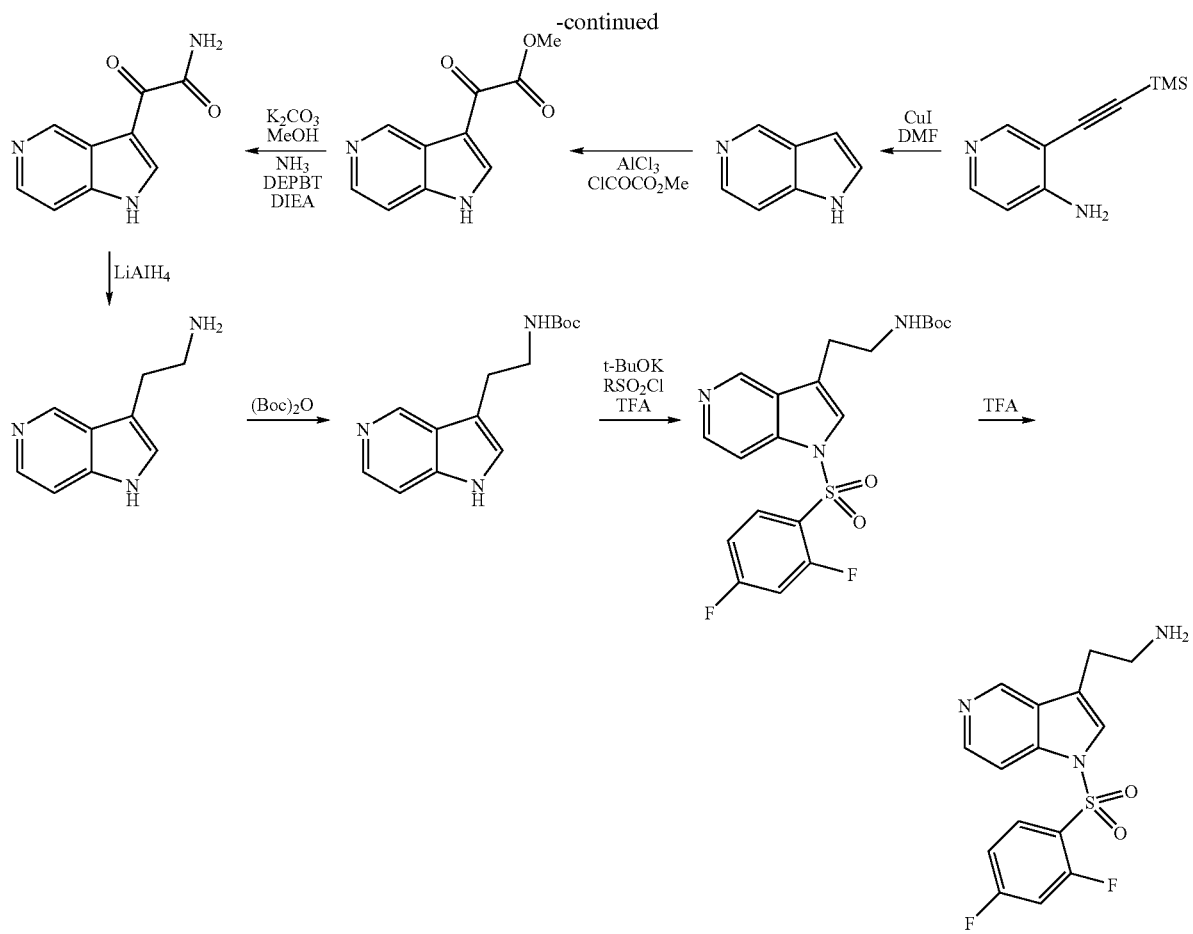

Step 1. Preparation of 2,2-DIMETHYL-N-PYRIDIN-4-YL-PROPIONAMIDE

A solution of pivaloyl chloride (1.1 eq.) in $CH_2Cl_2$ is added to a solution of 4-aminopyridine (1 eq.) and triethylamine (1.2 eq.) in $CH_2Cl_2$, stirred at 0° C. for 2 h, washed with aqueous sodium bicarbonate, dried over $MgSO_4$ and concentrated in vacuo. The resultant residue is purified by flash chromatography over silica gel to afford the title propionamide compound.

Step 2. Preparation of 3-2,2-DIMETHYL-N-(3-IODOPYRIDIN-4-YL) PROPIONAMIDE

A suspension of 2,2-dimethyl-N-pyridin-4-yl-propionamide (1 eq.) in a mixture of THF and TMEDA (2.6 eq) at −78° C. is treated with n-butyllithium (2.6 eq.), warmed to −10° C. for 2 h, cooled to −78°, treated with a solution of iodine (2.6 eq.) in THF, stirred at −78° for 2 h, warmed to 0° C. and quenched with saturated potassium thiosulfate solution. The phases are separated; the organic phase is dried over $MgSO_4$ and concentrated in vacuo to afford the title iodo compound.

Step 3. Preparation of 2,2-DIMETHYL-N-{[(3-TRIMETHYLSILANYL)ETHYNYL]PYRIDIN-4-YL}PROPIONAMIDE A mixture of 3-2,2-dimethyl-N-(3-iodopyridin-4-yl)propionamide (1.0 eq.) trimethylsilylacetylene (1.8 eq.), $PdCl_2$ $(PPh_3)_2$ (0.05 eq.), CuI (0.1 eq.) and triethylamine (3.5 eq.) is heated to 100° C. in a sealed tube for 10 hours. The solvent is removed under vacuum, and the residue is partitioned between EtOAc and water. The organic phase is dried over $MgSO_4$ and concentrated in vacuo to give the title ethynyl compound which is used without further purification in step 4, below.

Step 4. Preparation of {[(3-TRIMETHYLSILANYL)ETHYNYL]-PYRIDIN-4-YL}AMINE

The compound obtained in step 3 hereinabove is treated with 10% sulfuric acid at reflux temperature for 15 h, then basified with 50% NaOH solution and extracted with ethyl acetate. The organic layers are dried over $MgSO_4$ and concentrated. Purification of the resultant residue by flash chromatography (silica gel, $CH_2Cl_2$/methanol as eluent) gives the title pyridinylamine compound.

Step 5. Preparation of 5-AZAINDOLE

A solution of {[(3-trimethylsilanyl)ethynyl]pyridin-4-yl}amine in DMF is treated with cuprous iodide (2 eq.), stirred at reflux temperature for 2 h, cooled to room temperature, diluted with EtOAc, filtered through celite and concentrated in vacuo. The residue is purified by flash chromatography (silica gel, EtOAc/hexane as eluent) to afford the title 5-azaindole compound.

Step 6. Preparation of METHYL OXO-(1H-PYRROLO[3,2-C]-PYRIDIN-3-YL) ACETATE

A suspension of aluminum chloride (5 eq.) in $CH_2Cl_2$ is treated with 5-azaindole (1 eq.), stirred at room temperature for 1 h, treated dropwise with methyl chlorooxoacetate (5 eq.), stirred for 8 h, quenched by cautious addition of methanol and concentrated in vacuo. The resultant residue is purified by chromatography over silica gel to afford the title acetate compound.

Step 7. Preparation of 2-OXO-2-(1H-PYRROLO[3,2-C]PYRIDIN-3-YL)-ACETAMIDE

A mixture of methyl oxo-(1H-pyrrolo[3,2-c]-pyridin-3-yl) acetate (1 eq.) and $K_2CO_3$ (2 eq.) in methanol is stirred at room temperature for 8 h and filtered. The filtercake is air-dried to give potassium 5-azaindole 3-glyoxylate. A mixture of this glyoxylate salt, ammonia (solution in dioxane (5 eq.), 3-(diethoxyphosphoryloxy)-1,2,3-benzotriazin-4(3H)-one (DEPBT) (1 eq.) and diisopropylethylamine (DIEA) in DMF is stirred for 8 h, diluted with EtOAc and aqueous sodium carbonate. The organic phase is separated, dried over $MgSO_4$ and concentrated in vacuo. The resultant residue is purified over silica gel with EtOAc/MeOH as eluent to afford the title compound.

Step 8 Preparation of 2-(1H-PYRROLO[3,2-C]PYRIDIN-3-YL)-ETHYLAMINE

A solution of 2-oxo-2-(1H-pyrrolo[3,2-c]pyridin-3-yl)-acetamide (1 eq.) in ether is treated with lithium aluminum hydride (4 eq.), refluxed for 8 h, cooled to 0° C. and quenched by addition of Rochelle's salt solution. The reaction mixture is extracted with $CH_2Cl_2$. The extracts are combined dried over $MgSO_4$ and concentrated in vacuo to give the title amine product, which is used as is in step 9, below.

Step 9. Preparation of T-BUTYL [2-(1H-PYRROLO [3,2-C]PYRIDIN-3-YL)-ETHYL]-CARBAMATE (BOC-5-AZATRYPTAMINE)

A solution of 2-(1H-pyrrolo[3,2-c]pyridin-3-yl)-ethylamine (1 eq.) in 1:1 acetone/water is treated with di-t-butyl dicarbonate (1.1 eq.) and potassium carbonate (1.2 eq.), stirred at room temperature for 16 h, concentrated to remove the acetone, and extracted with EtOAc. The extracts are combined, dried over MgSO4 and concentrated in vacuo. The resultant residue is purified by crystallization from EtOAc/hexane to afford the title protected azatryptamine.

Step 10. Preparation of {2-{1-[(2,4-DIFLUOROPHENYL)-SULFONYL]-1H-PYRROLO[3,2-C] PYRIDIN-3-YL}ETHYL}CARBAMATE A mixture of Boc-5-azatryptamine (1.1 eq.) and 2,4-difluorophenylsulfonyl chloride (1.0 eq.) in THF at room temperature is treated portionwise with solid potassium t-butoxide (1.2 eq), stirred at room temperature for 16 h, poured into saturated $NaHCO_3$ and extracted with EtOAc. The extracts are combined, dried over $MgSO_4$ and concentrated in vauo. Purification of the resultant residue by column chromatography (silica gel, EtOAc/Hexanes as eluent) affords the title carbamate product.

Step 11. Preparation of 2-{1-[(2,4-DIFLUOROPHENYL)-SULFONYL]-1H-PYRROLO[3,2-C]PYRIDIN-3-YL}ETHYLAMINE A solution of {2-{1-[(2,4-difluorophenyl)sulfonyl]-1H-pyrrolo[3,2-c]pyridin-3-yl}ethyl}carbamate in $CH_2Cl_2$ is treated with trifluoroacetic acid, stirred for 2 h and concentrated in vacuo. The resultant residue is purified by preparative reverse phase HPLC to afford the title product.

EXAMPLES 37-55

Preparation of 2-[1-(Substituted sulfonyl)-1H-pyrrolo[3,2-c]pyridin-3-yl]-ethylamine Derivatives Using essentially the same procedures as described for Examples 35 and 36, and employing the appropriate amine in step 7 of Example 36 and the appropriate sulfonyl chloride in step 7 of Example 35 or step 10 of Example 36, the compounds shown in Table II are prepared and purified by preparative reverse phase HPLC using the following HPLC conditions: HP 1100 HPLC system; Waters Xterra MS C18, 2 mm (i.d.)×50 mm (length), 3.5 □m column, set at 50° C.; Flow rate 1.0 mL/min; Solvent A: 0.02% formic acid in water; Solvent B 0.02% formic acid in ACN; Gradient: Time O: 10% B; 2.5 min 90% B; 3 min 90% B; Sample concentration: ~2.0 mM; Injection volume: 5 uL; Detection: 220 nm, 254 nm DAD.

TABLE II

| Ex. No. | $R_5$ | $R_6$ | $R_{10}$ | M + H | HPLC Min |
|---|---|---|---|---|---|
| 37 | H | H | 1-methyl-1H-imidazol-4-yl | — | — |
| 38 | H | H | 3,5-dimethyl-isoxazol-4-yl | — | — |
| 39 | H | H | imidazo[2,1-b]thiazol-5-yl | 348 | 1.81 |
| 40 | H | H | 3-chlorophenyl | 336 | 2.2 |
| 41 | H | H | 3-fluorophenyl | 320 | 2.09 |
| 42 | H | H | 3-methoxyphenyl | 332 | 2.09 |
| 43 | H | H | 5-chlorothiophen-2-yl | 342 | 2.24 |
| 44 | H | H | phenyl | 302 | 1.84 |
| 45 | H | H | 3-methylphenyl | 316 | 2.16 |
| 46 | H | H | 3-(trifluoromethyl)phenyl | 370 | 2.36 |
| 47 | H | H | 2,3-dichlorophenyl | 370 | 2.06 |
| 48 | H | $CH_3$ | 5-chlorothiophen-2-yl | — | — |
| 49 | H | $CH_3$ | naphth-2-yl | — | — |
| 50 | H | $CH_3$ | quinolin-8-yl | — | — |
| 51 | H | $CH_3$ | 5-chloro-1,3-dimethyl-1H-pyrazol-4-yl | — | — |
| 52 | $CH_3$ | $CH_3$ | benzo[1,2,5]thiadiazol-4-yl | — | — |
| 53 | $CH_3$ | $CH_3$ | 7-chlorobenzo[1,2,5]oxadiazol-4-yl | — | — |
| 54 | $CH_3$ | $CH_3$ | 6-chloroimidazo[2,1-b]thiazol-5-yl | — | — |
| 55 | $CH_3$ | $CH_3$ | 5-chloro-3-methyl-benzo[b]thiophene-2-yl | — | — |

EXAMPLE 56

Preparation of 2-{1-[(3-Methoxyphenyl)sulfonyl]-1H-pyrrolo[2,3-c]pyridin-3-yl}ethylamine

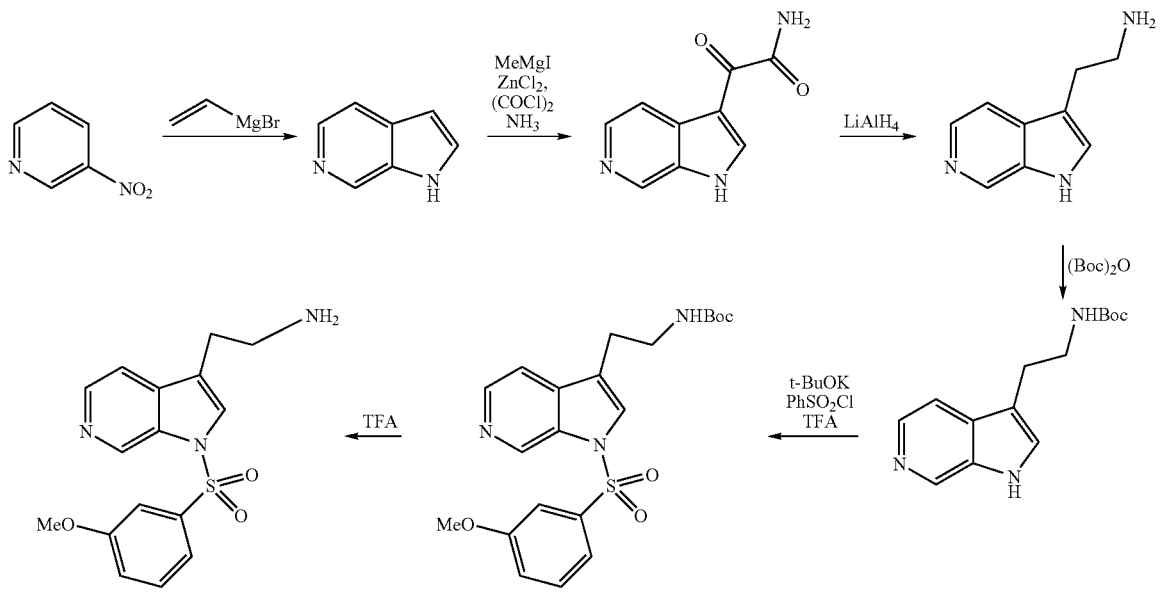

Step 1. Preparation of 6-AZAINDOLE

A solution of 3-nitropyridine in THF at −78° C. is treated with vinyl magnesium bromide (3 eq), stirred at −20° C. for 8 h and quenched with 20% ammonium chloride. The phases are separated and the aqueous phase is extracted with EtOAc. The organic phase and the combined extracts are mixed together, dried over MgSO$_4$ and concentrated in vacuo. The resultant residue is chromatographed over silica gel to afford the title 6-azaindole.

Step 2. Preparation of 2-OXO-2-(1H-PYRROLO[2,3-C]-PYRIDIN-3-YL) ACETAMIDE

A solution of 6-azaindole (1.0 eq.) in ether is treated with methyl magnesium iodide (1.1 eq.) at room temperature, stirred for 1 h, treated with zinc chloride (1.2 eq), stirred for a further 1 h, treated with oxalyl chloride (10 eq.), stirred for 10 h and concentrated in vacuo to remove the solvent and excess oxalyl chloride. The resultant residue is dissolved in CH$_3$CN and pyridine (1.6 eq.), treated with ammonia (2 eq., solution in dioxane), stirred for 1 h and concentrated in vacuo. This residue is purified by chromatography [silica gel, CH$_2$Cl$_2$/methanol (containing 5% ammonium hydroxide) as eluent] to afford the title acetamide compound.

Step 3. Preparation of 6-AZATRYPTAMINE

A solution of 2-oxo-2-(1H-pyrrolo[2,3-c]pyridin-3-yl)acetamide (1 eq.) in ether is treated with lithium aluminum hydride (4 eq.), heated at reflux temperature for 8 h, cooled to 0° C. and quenched by addition of Rochelle's salt solution. The reaction mixture is extracted with CH$_2$Cl$_2$; the combined extracts are dried over MgSO$_4$ and concentrated in vacuo to afford the title 6-azatryptamine product, which is used directly in step 4, below.

Step 4. Preparation of N-T-BUTYLOXYCARBONYL 6-AZATRYPTAMINE (BOC-6-AZATRYPTAMINE)

A solution of 6-azatryptamine (1.0 eq.) in 1:1 acetone/water is treated with di-t-butyl dicarbonate (1.1 eq.) and potassium carbonate (1.2 eq.), stirred at room temperature for 16 h, concentrated in vacuo to remove the acetone and extracted with EtOAc. The extracts are combined, dried over MgSO$_4$ and concentrated. This concentrate is purified by crystallization from EtOAc/hexanes to afford the title protected amine.

Step 5. Preparation of T-BUTYL [2-{1-(3-METHOXYBENZENESULFONYL)-1H-PYRROLO[2,3-C]PYRIDIN-3-YL}-ETHYL]CARBAMATE A mixture of Boc-6-azatryptamine (1.1 eq.) and 3-methoxybenzenesulfonyl chloride (1.0 eq.) in THF at room temperature is treated portionwise with solid potassium t-butoxide (1.2 eq), stirred at room temperature for 16 h, poured into saturated NaHCO$_3$ and extracted with EtOAc. The combined extracts are dried over MgSO$_4$ and concentrated in vacuo. Chromatographic purification of this concentrate using silica gel and EtOAc/Hexanes as eluent gives the title sulfonated compound.

Step 6. Preparation of 2-{1-(3-METHOXYBENZENESULFONYL)-1H-PYRROLO[2,3-C]PYRIDIN-3-YL}ETHYLAMINE A solution of t-Butyl [2-{1-(3-methoxybenzene-sulfonyl)-1H-pyrrolo[2,3-c]pyridin-3-yl}-ethyl]carbamate in CH$_2$Cl$_2$ is treated with trifluoroacetic acid, stirred for 2 h and concentrated in vacuo. The resultant residue is purified by preparative reverse phase HPLC to afford the title final product.

EXAMPLES 57-67

Preparation of 2-[1-substituted-sulfonyl)-1H-pyrrolo[2,3-c]pyridin-3-yl]-ethylamine derivatives Using essentially the same procedures described for Example 56, and employing the appropriate amine in step 2 and sulfonyl chloride in step 5, the compounds shown in Table III are prepared and purified by preparative reverse phase HPLC.

TABLE III

| Ex. No. | $R_5$ | $R_6$ | $R_{10}$ |
|---|---|---|---|
| 57 | H | H | 1-methyl-1H-imidazol-4-yl |
| 58 | H | H | 3,5-dimethyl-isoxazol-4-yl |
| 59 | H | H | 2,4-difluorophenyl |
| 60 | H | $CH_3$ | 5-chlorothiophene-2-yl |
| 61 | H | $CH_3$ | naphth-2-yl |
| 62 | H | $CH_3$ | quinolin-8-yl |
| 63 | H | $CH_3$ | 5-chloro-1,3-dimethyl-1H-pyrazol-4-yl |
| 64 | $CH_3$ | $CH_3$ | benzo[1,2,5]thiadiazol-4-yl |
| 65 | $CH_3$ | $CH_3$ | 7-chlorobenzo[1,2,5]oxadiazol-4-yl |
| 66 | $CH_3$ | $CH_3$ | 6-chloroimidazo[2,1-b]thiazol-5-yl |
| 67 | $CH_3$ | $CH_3$ | 5-chloro-3-methyl-benzo[b]thiophen-2-yl |

EXAMPLE 68

Preparation of 2-[1-(3-Methoxybenzenesulfonyl)-1H-pyrrolo[2,3-b]pyridin-3-yl]ethylamine

Step 1. Preparation of 2-CHLORO-1-(1H-PYRROLO[2,3-B]-PYRIDIN-3-YL)ETHANONE

A mixture of 7-azaindole (10 g) and chloroacetyl chloride (7.4 mL, 1.1 eq.) are dissolved in carbon disulfide, treated with aluminum chloride (85 g, 7.5 eq.), heated at reflux temperature for 2 h, treated with chloroacetyl chloride (7.4 mL, 1.1 eq.), continued heating at reflux temperature for a further 2 h, cooled to room temperature and decanted to remove the solvent. The sediment is cooled to 0° C., quenched with ice water, treated with sodium carbonate to pH 9 and extracted with EtOAc. The extracts are combined, dried over MgSO4 and concentrated in vacuo to give the title ethanone, 12.5 g (75% yield), identified by HPLC and mass spectral analyses.

Step 2. Preparation of 3-(2-CHLOROETHYL)-1H-PYRROLO-[2,3-B]PYRIDINE

A stirred solution of 2-chloro-1-(1H-pyrrolo[2,3-b]pyridin-3-yl)ethanone (12.5 g) in TFA at room temperature is treated with triethylsilane (72 mL, 7 eq.), stirred for 16 h, diluted with EtOAc and saturated sodium carbonate to pH 8. The phases are separated and the organic phase is dried over $MgSO_4$ and concentrated in vacuo. The resultant residue is purified by flash chromatography (silica gel, 10% EtOAc in ether as eluent) to give the title pyrrolo[2,3-b]pyridine compound, identified by NMR and mass spectral analyses.

Step 3. Preparation of 2-(1H-PYRROLO[2,3-B]PYRIDIN-3-YL)ETHYLAMINE

A mixture of 3-(2-Chloroethyl)-1H-pyrrolo[2,3-b]pyridine (4.0 g) and sodium iodide (3.2 g, 0.95 eq.) in a solution of ammonia in methanol (7 N, 20 mL) is heated to 60° C. in a Fischer-Porter sealed pressure bottle for 48 h. The bottle is cooled, opened cautiously and the solvent removed in vacuo. The resultant residue is recrystallized from THF to give the title ethylamine compound as a tan solid, 4.8 g, identified by HPLC and mass spectral analyses.

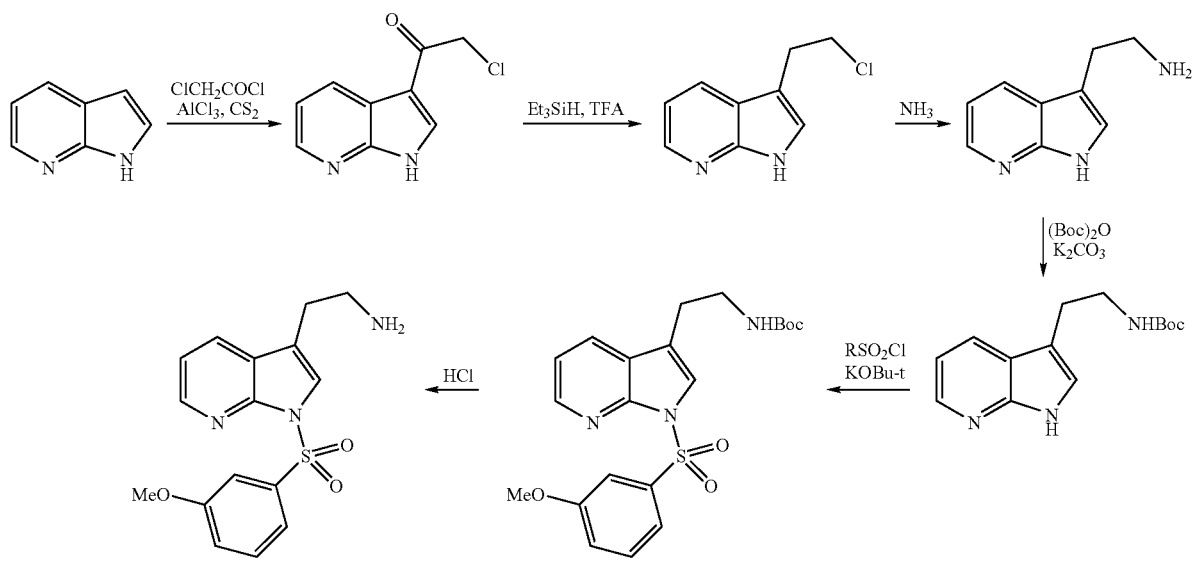

Step 4. Preparation of N-T-BUTYLOXYCARBONYL 7-AZATRYPTAMINE

A solution of 7-azatryptamine (3.6 g) in 1:1 acetone/water is treated with di-t-butyl dicarbonate (5.4 g, 1.1 eq.) and potassium carbonate (9.3 g, 2 eq.), stirred at room temperature for 16 h, concentrated to remove the acetone and extracted with EtOAc. The extracts are combined, dried over $MgSO_4$ and concentrated in vacuo. The resultant residue is purified by flash chromatography (silica gel, 30% EtOAc in ether as eluent) to give the title protected-7-azatryptamine, 2.0 g, identified by HPLC and mass spectral analyses.

Step 5. Preparation of T-BUTYL {2-{[1-(3-METHOXYBENZENE) SULFONYL]-1H-PYRROLO[2,3-B]PYRIDIN-3-YL}ETHYL}CARBAMATE A solution of N-t-butyloxycarbonyl-7-azatryptamine (52.2 mg, 1.1 eq.) and 3-methoxybenzenesulfonyl chloride (51 mg, 1.1 eq.) in THF, is treated with potassium t-butoxide (1.0 M solution in THF, 1.2 eq, 0.24 mL), stirred at room temperature for 16 h and concentrated in vacuo. The resultant residue is used as is in step 6, below.

Step 6. Preparation of 2-{1-(3-METHOXYBENZENESULFONYL)-1H-PYRROLO[2,3-B]PYRIDIN-3-YL}-ETHYLAMINE A solution of t-Butyl {2-{[1-(3-methoxybenzene)sulfonyl]-1H-pyrrolo[2,3-b]pyridin-3-yl}ethyl}carbamate in THF, is treated with 4 N HCl in methanol, stirred for 2 h and concentrated in vacuo. The resultant residue is purified by preparative reverse phase HPLC[1], M+H 332, 2.17 min.

[1]HPLC Conditions are the same as those used in Table I.

EXAMPLES 69-158

Preparation of 2-[1-Substituted-sulfonyl)-1H-pyrrolo-[2,3-b]pyridin-3-yl]ethylamine Derivatives Using essentially the same procedures described in Example 68 and employing the appropriate amine in step 3 and appropriate sulfonyl chloride in step 5, the compounds shown in Table IV are prepared and purified by preparative reverse phase HPLC using the same HPLC conditions described for Table I.

TABLE IV

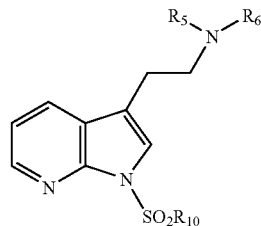

| Ex. No. | $R_5$ | $R_6$ | $R_{10}$ | M + H | HPLC Min |
|---|---|---|---|---|---|
| 69 | H | H | 1-methyl-1H-imidazol-4-yl | — | — |
| 70 | H | H | 3,5-dimethyl-isoxazol-4-yl | 321 | 1.69 |
| 71 | H | H | 2,4-difluorophenyl | 338 | 1.66 |
| 72 | H | $CH_3$ | 5-chlorothiophene-2-yl | — | — |
| 73 | H | $CH_3$ | naphth-2-yl | — | — |
| 74 | H | $CH_3$ | quinolin-8-yl | — | — |
| 75 | H | $CH_3$ | 5-chloro-1,3-dimethyl-1H-pyrazol-4-yl | — | — |
| 76 | $CH_3$ | $CH_3$ | benzo[1,2,5]thiadiazol-4-yl | — | — |
| 77 | $CH_3$ | $CH_3$ | 7-chlorobenzo[1,2,5]oxadi-azol-4-yl | — | — |
| 78 | $CH_3$ | $CH_3$ | 6-chloroimidazo[2,1-b]thiazol-5-yl | — | — |
| 79 | $CH_3$ | $CH_3$ | 5-chloro-3-methyl-benzo[b]thiophene-2-yl | — | — |
| 80 | H | H | phenyl | 302 | 1.74 |
| 81 | H | H | benzyl | 316 | 1.91 |
| 82 | H | H | 2-naphthyl | 352 | 2.41 |
| 83 | H | H | 4-aminophenyl | 317 | 1.58 |
| 84 | H | H | 4-methoxyphenyl | 332 | 2.15 |
| 85 | H | H | 3,4-dimethoxyphenyl | 362 | 2.05 |
| 86 | H | H | 4-(trifluoromethoxy)phenyl | 386 | 2.54 |
| 87 | H | H | 2-cyanophenyl | 327 | 2.06 |
| 88 | H | H | 4-cyanophenyl | 327 | 2.05 |
| 89 | H | H | 2-(trifluoromethyl)phenyl | 370 | 2.36 |
| 90 | H | H | 3-(trifluoromethyl)phenyl | 370 | 2.46 |
| 91 | H | H | 4-t-butylphenyl | 358 | 2.79 |
| 92 | H | H | 3,5-bis-(trifluoromethyl)-phenyl | 438 | 2.78 |
| 93 | H | H | 4-i-propylphenyl | 344 | 2.63 |
| 94 | $CH_3$ | $CH_3$ | phenyl | 330 | 2.56 |
| 95 | $CH_3$ | $CH_3$ | benzyl | 344 | 2.53 |
| 96 | $CH_3$ | $CH_3$ | 2-naphthyl | 380 | 3.19 |
| 97 | $CH_3$ | $CH_3$ | 3-methoxyphenyl | 360 | 2.67 |
| 98 | $CH_3$ | $CH_3$ | 4-methoxyphenyl | 360 | 2.63 |
| 99 | $CH_3$ | $CH_3$ | 3,4-dimethoxyphenyl | 390 | 1.52 |
| 100 | $CH_3$ | $CH_3$ | 4-(trifluoromethoxy)phenyl | 414 | 3.03 |
| 101 | $CH_3$ | $CH_3$ | 2-cyanophenyl | 355 | 2.45 |
| 102 | $CH_3$ | $CH_3$ | 4-cyanophenyl | 355 | 2.45 |
| 103 | $CH_3$ | $CH_3$ | 2-(trifluoromethyl)phenyl | 398 | 2.82 |
| 104 | $CH_3$ | $CH_3$ | 3-(trifluoromethyl)phenyl | 398 | 2.98 |
| 105 | $CH_3$ | $CH_3$ | 4-t-butylphenyl | 387 | 1.96 |
| 106 | $CH_3$ | $CH_3$ | 3,5-bis-(trifluoromethyl)-phenyl | 366 | 2.45 |
| 107 | H | H | 4-(trifluoromethyl)phenyl | 370 | 1.83 |
| 108 | H | H | 2,5-dimethylphenyl | 330 | 1.84 |
| 109 | H | H | 3-chloro-4-fluorophenyl | 354 | 1.87 |
| 110 | H | H | 2-chloro-4-fluorophenyl | 354 | 1.78 |
| 111 | H | H | 3-chloro-4-methylphenyl | 350 | 1.93 |
| 112 | H | H | 3-fluoro-6-methylphenyl | 334 | 1.81 |
| 113 | H | H | 3-chloro-6-methoxyphenyl | 366 | 1.81 |
| 114 | H | H | 4-chloro-2,5-dimethyl-phenyl | 364 | 2.09 |
| 115 | H | H | 2-fluorophenyl | 320 | 1.6 |
| 116 | H | H | 3-fluorophenyl | 320 | 1.67 |
| 117 | H | H | 4-fluorophenyl | 320 | 1.66 |
| 118 | H | H | 3,4-difluorophenyl | 338 | 1.75 |
| 119 | H | H | 2,3,4-trifluorophenyl | 356 | 1.75 |
| 120 | H | H | 2-chlorophenyl | 336 | 1.69 |
| 121 | H | H | 3-chlorophenyl | 336 | 1.8 |
| 122 | H | H | 4-chlorophenyl | 336 | 1.82 |
| 123 | H | H | 2,3-dichlorophenyl | 371 | 1.88 |
| 124 | H | H | 2,5-dichlorophenyl | 371 | 1.92 |
| 125 | H | H | 3,4-dichlorophenyl | 371 | 2.02 |
| 126 | H | H | 3,5-dichlorophenyl | 371 | 2.01 |
| 127 | H | H | 2,4,5-trichlorophenyl | 405 | 2.14 |
| 128 | H | H | 2,4,6-trichlorophenyl | 405 | 2.1 |
| 129 | H | H | 5-chloro-thiophene-2-yl | 342 | 1.79 |
| 130 | H | H | 5-bromo-thiophene-2-yl | 387 | 1.83 |
| 131 | H | H | 4,5-dichlorothiophen-2-yl | 376 | 2.01 |
| 132 | H | H | 2,5-dichlorothiophen-3-yl | 376 | 1.93 |
| 133 | H | H | 4,5-dibromothiophen-2-yl | 466 | 2.05 |
| 134 | H | H | 3-bromo-5-chlorothiophen-2-yl | 420 | 1.96 |

TABLE IV-continued

R5-N-R6 on pyrrolopyridine with SO2R10

| Ex. No. | R5 | R6 | R10 | M + H | HPLC Min |
|---|---|---|---|---|---|
| 135 | H | H | 4-bromo-5-chlorothiophen-2-yl | 420 | 2.04 |
| 136 | H | H | 3-bromo-2,5-dichlorothio-phen-4-yl | 456 | 2.11 |
| 137 | H | H | 2-chloroimidazo[1,2-a]-pyridin-3-yl | 376 | 1.74 |
| 138 | H | H | 2-acetylamino-4-methylthi-azol-5-yl | 380 | 1.53 |
| 139 | H | H | 1,2-dimethyl-1H-imidazol-4-yl | 320 | 1.29 |
| 140 | H | H | 5-chloro-1,3-dimethyl-1H-pyrazol-4-yl | 354 | 1.61 |
| 141 | H | H | benzo[1,2,5]oxadiazol-4-yl | 344 | 1.61 |
| 142 | H | H | benzo[1,2,5]thiadiazol-4-yl | 360 | 1.61 |
| 143 | CH3 | CH3 | 4-(trifluoromethyl)phenyl | 398 | 2.09 |
| 144 | CH3 | CH3 | 2-chloro-4-fluorophenyl | 382 | 1.96 |
| 145 | CH3 | CH3 | 3-chloro-6-methoxyphenyl | 394 | 2.01 |
| 146 | CH3 | CH3 | 4-chloro-2,5-dimethyl-phenyl | 392 | 2.32 |
| 147 | CH3 | CH3 | 2-fluorophenyl | 348 | 1.77 |
| 148 | CH3 | CH3 | 3-fluorophenyl | 348 | 1.87 |
| 149 | CH3 | CH3 | 3,4-difluorophenyl | 366 | 1.95 |
| 150 | CH3 | CH3 | 2,3,4-trifluorophenyl | 384 | 1.95 |
| 151 | CH3 | CH3 | 5-chlorothiophen-2-yl | 370 | 2 |
| 152 | CH3 | CH3 | 2,5-dichlorothiophen-3-yl | 405 | 2.16 |
| 153 | CH3 | CH3 | 2-chloro-imidazo[1,2-a]-pyridin-3-yl | 404 | 1.96 |
| 154 | H | H | 6-chloroimidazo[2,1-b]thi-azol-5-yl | 382 | 2.32 |
| 155 | H | H | imidazo[2,1-b]thiazol-5-yl | 348 | 2.10 |
| 156 | H | H | 3-methylphenyl | 316 | 2.36 |
| 157 | H | H | 3-bromophenyl | 381 | 2.48 |
| 158 | H | H | 2,6-dichloroimidazo-[2,1-b]-thiazol-5-yl | 417 | 2.61 |

EXAMPLE 159

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table V, below.

TABLE V

| Test Compound (Ex. No.) | 5-HT6 Binding Ki (nM) |
|---|---|
| 1 | 5.0 |
| 5 | 2.0 |
| 11 | 0.8 |
| 13 | 5.0 |
| 14 | 15.0 |
| 15 | 16.0 |
| 16 | 1.6 |
| 17 | 2.9 |
| 18 | 1.6 |
| 19 | 4.5 |
| 20 | 3.3 |
| 21 | 0.6 |
| 22 | 2.4 |
| 23 | 2.1 |
| 24 | 5.3 |
| 25 | 3.5 |

TABLE V-continued

| Test Compound (Ex. No.) | 5-HT6 Binding Ki (nM) |
|---|---|
| 26 | 7.3 |
| 35 | 15.7 |
| 39 | 47.0 |
| 40 | 110.3 |
| 41 | 170.3 |
| 42 | 198.0 |
| 43 | 47.5 |
| 44 | 164.3 |
| 45 | 151.7 |
| 46 | 173.0 |
| 47 | 32.7 |
| 68 | 33.3 |
| 71 | 113.3 |
| 80 | 43.0 |
| 82 | 12.0 |
| 83 | 2.4 |
| 84 | 74.6 |
| 85 | 106.0 |
| 87 | 79.0 |
| 89 | 38.3 |
| 90 | 21.0 |
| 91 | 114.3 |
| 93 | 39.3 |
| 94 | 40.0 |
| 96 | 19.6 |
| 97 | 24.6 |
| 99 | 76.6 |
| 103 | 38.0 |
| 104 | 29.3 |
| 105 | 60.3 |
| 108 | 23.7 |
| 109 | 61.3 |
| 110 | 38.3 |
| 111 | 3.6 |
| 112 | 38.7 |
| 113 | 185.7 |
| 114 | 17.7 |
| 115 | 39.3 |
| 116 | 13.4 |
| 118 | 89.3 |
| 120 | 27.0 |
| 121 | 6.0 |
| 122 | 50.0 |
| 123 | 2.5 |
| 124 | 72.7 |
| 125 | 20.3 |
| 126 | 16.3 |
| 127 | 106.3 |
| 128 | 24.0 |
| 129 | 11.7 |
| 130 | 8.5 |
| 131 | 19.7 |
| 132 | 52.0 |
| 133 | 10.7 |
| 134 | 29.0 |
| 135 | 16.3 |
| 136 | 40.0 |
| 137 | 25.0 |
| 141 | 42.3 |
| 142 | 69.7 |
| 144 | 56.3 |
| 146 | 31.7 |
| 147 | 47.3 |
| 148 | 28.0 |
| 151 | 13.0 |
| 152 | 53.7 |
| 153 | 57.3 |
| 154 | 7.4 |
| 157 | 5.6 |
| 158 | 90.7 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention have a significantly high degree of affinity for the serotonin 5-HT6 receptor.

What is claimed is:

1. A method for the treatment of a disorder selected from Alzheimer's disease, or memory loss in a patient in need thereof which comprises providing to said patient a therapeutically effective amount of a compound of formula I

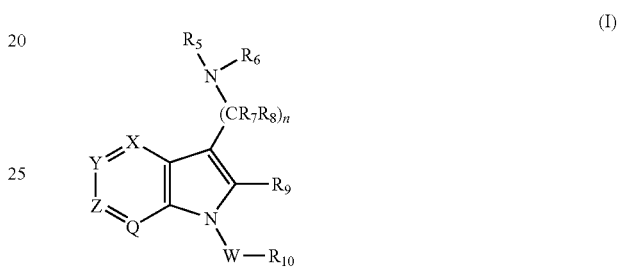

wherein
W is $SO_2$, CO, $CONR_{11}$ or $CSNR_{12}$;
X is N or $CR_1$;
Y is N or $CR_2$;
Z is N or $CR_3$;
Q is N or $CR_4$ with the proviso that only one of X, Y, Z and Q is N;
n is an integer of 2 or 3;
$R_1$, $R_2$, $R_3$ and $R_4$ are each independently H, halogen, CN, $OCO_2R_{13}$, $CO_2R_{14}$, $CONR_{15}R_{16}$, $CNR_{17}NR_{18}R_{19}$, $SO_mR_{20}$, $NR_{21}R_{22}$, $OR_{23}$, $COR_{24}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_5$ and $R_6$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;
$R_7$ and $R_8$ are each independently H or an optionally substituted $C_1$-$C_6$alkyl group;
$R_9$ is H, halogen, or a $C_1$-$C_6$alkyl, $C_1$-$C_6$alkoxy, aryl or heteroaryl group each optionally substituted;
$R_{10}$ is an optionally substituted $C_1$-$C_6$alkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S with the proviso that when Q is N and X, Y and Z are CH then $R_{10}$ must be other than phenyl;
m is 0 or an integer of 1 or 2;
$R_{11}$ and $R_{12}$ are each independently H or a $C_1$-$C_6$alkyl, aryl or heteroaryl group each optionally substituted;
$R_{13}$, $R_{14}$, $R_{20}$, $R_{23}$ and $R_{24}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{15}$, $R_{16}$ are each independently H or an optionally substituted $C_1$-$C_6$alkyl group; and $R_{17}$, $R_{18}$, $R_{19}$, $R_{21}$ and $R_{22}$ are each independently H or an optionally substituted $C_1$-$C_4$alkyl group; or $R_{21}$ and $R_{22}$ may be taken together with the atom to which they are attached to form a 5- to 7-membered ring optionally containing another heteroatom selected from O, N or S; or the stereoisomers thereof or the pharmaceutically acceptable salts thereof.

2. The method according to claim 1 having a formula I compound wherein W is $SO_2$.

3. The method according to claim 1 having a formula I compound wherein W is $SO_2$; n is 2 and $R_9$ is H.

4. The method according to claim 1 having a formula I compound wherein W is $SO_2$; X is N; Y is $CR_2$; Z is $CR_3$; and Q is $CR_4$.

5. The method according to claim 1 having a formula I compound wherein W is $SO_2$; X is $CR_1$; Y is $CR_2$; Z is $CR_3$ and Q is N.

6. The method according to claim 1 having a formula I compound selected from the group consisting of:

2-[1-(2-chlorobenzenesulfonyl)-1H-pyrrolo[3,2-b]pyridin-3-yl]ethylamine;
2-{1-[(6-chloroimidazo[2,1-b]thiazol-5-yl)sulfonyl]-1H-pyrrolo[3,2-b]pyridin-3-yl}ethylamine;
2-{1-[(5-chlorothiophen-2-yl)sulfonyl]-1H-pyrrolo[3,2-b]pyridin-3-yl}ethylamine;
2-{1-[(3-trifluoromethylbenzene)sulfonyl]-1H-pyrrolo[3,2-b]pyridin-3-yl}ethylamine;
2-{1-[(2-chloro-4-trifluoromethylbenzene)sulfonyl]-1H-pyrrolo[3,2-b]pyridin-3-yl}ethylamine;
2-{1-[(3,4-difluorobenzene)sulfonyl]-1H-pyrrolo[3,2-b]pyridin-3-yl}ethylamine;
2-[1-(3-chlorobenzenesulfonyl)-1H-pyrrolo[3,2-b]pyridin-3-yl]ethylamine;
2-[1-(3-methoxybenzenesulfonyl)-1H-pyrrolo[3,2-b]pyridin-3-yl]ethylamine;
2-{1-[(imidazo[2,1-b]thiazol-5-yl)sulfonyl]-1H-pyrrolo[3,2-b]pyridin-3-yl}ethylamine;
[1-(benzenesulfonyl)-1H-pyrrolo[3,2-b]pyridin-3-yl]ethylamine;
2-[1-(3-fluorobenzenesulfonyl)-1H-pyrrolo[3,2-b]pyridin-3-yl]ethylamine;
2-[1-(4-aminobenzenesulfonyl)-1H-pyrrolo[3,2-b]pyridin-3-yl]ethylamine;
2-[1-(3-methylbenzenesulfonyl)-1H-pyrrolo[3,2-b]pyridin-3-yl]ethylamine;
2-[1-(2,3-dichlorobenzenesulfonyl)-1H-pyrrolo[3,2-b]pyridin-3-yl]ethylamine;
2-[1-(2-fluorobenzenesulfonyl)-1H-pyrrolo[3,2-b]pyridin-3-yl]ethylamine;
2-[1-(3-bromobenzenesulfonyl)-1H-pyrrolo[3,2-b]pyridin-3-yl]ethylamine;
2-{1-[(2,6-dichloroimidazo[2,1-b]thiazol-5-yl)sulfonyl]-1H-pyrrolo[3,2-b]pyridin-3-yl}ethylamine;
2-{1-[(6-chloroimidazo[2,1-b]thiazol-5-yl)sulfonyl]-1H-pyrrolo[3,2-c]pyridin-3-yl}ethylamine;
2-[1-(4-chlorobenzenesulfonyl)-1H-pyrrolo[3,2-c]pyridin-3-yl]ethylamine;
2-{1-[(6-chloroimidazo[2,1-b]thiazol-5-yl)sulfonyl]-1H-pyrrolo[2,3-c]pyridin-3-yl}ethylamine;
2-[1-(4-chlorobenzenesulfonyl)-1H-pyrrolo[2,3-c]pyridin-3-yl]ethylamine;
2-[1-(2-naphthylsulfonyl)-1H-pyrrolo[2,3-b]pyridin-3-yl]ethylamine;
[1-(4-aminobenzenesulfonyl)-1H-pyrrolo[2,3-b]pyridin-3-yl]ethylamine;
{2-[1-(2-naphthylsulfonyl)-1H-pyrrolo[2,3-b]pyridin-3-yl]ethyl}methylamine;
{2-[1-(2-naphthylsulfonyl)-1H-pyrrolo[2,3-b]pyridin-3-yl]ethyl}dimethylamine;
2-{1-[(3-chloro-4-methylbenzene)sulfonyl]-1H-pyrrolo[2,3-b]pyridin-3-yl}ethylamine;
2-{1-[(4-chloro-2,5-dimethylbenzene)sulfonyl]-1H-pyrrolo[2,3-b]pyridin-3-yl}ethylamine;
2-[1-(3-fluorobenzenesulfonyl)-1H-pyrrolo[2,3-b]pyridin-3-yl]ethylamine;
2-[1-(3-chlorobenzenesulfonyl)-1H-pyrrolo[2,3-b]pyridin-3-yl]ethylamine;
2-[1-(2,3-dichlorobenzenesulfonyl)-1H-pyrrolo[2,3-b]pyridin-3-yl]ethylamine;
2-[1-(3,4-dichlorobenzenesulfonyl)-1H-pyrrolo[2,3-b]pyridin-3-yl]ethylamine;
2-[1-(3,5-dichlorobenzenesulfonyl)-1H-pyrrolo[2,3-b]pyridin-3-yl]ethylamine;
2-{1-[(5-chlorothiophen-2-yl)sulfonyl]-1H-pyrrolo[2,3-b]pyridin-3-yl}ethylamine;
2-{1-[(5-bromothiophen-2-yl)sulfonyl]-1H-pyrrolo[2,3-b]pyridin-3-yl}ethylamine;
2-{1-[(4,5-dichlorothiophen-2-yl)sulfonyl]-1H-pyrrolo[2,3-b]pyridin-3-yl}ethylamine;
2-{1-[(4,5-dibromothiophen-2-yl)sulfonyl]-1H-pyrrolo[2,3-b]pyridin-3-yl}ethylamine;
{1-[(4-bromo-5-chlorothiophen-2-yl)sulfonyl]-1H-pyrrolo[2,3-b]pyridin-3-yl}ethylamine;
{2-{1-[(5-chlorothiophen-2-yl)sulfonyl]-1H-pyrrolo[2,3-b]pyridin-3-yl}ethyl}dimethylamine;
2-{1-[(6-chloroimidazo[2,1-b]thiazol-5-yl)sulfonyl]-1H-pyrrolo[2,3-b]pyridin-3-yl}ethylamine;
2-[1-(3-methylbenzenesulfonyl)-1H-pyrrolo[2,3-b]pyridin-3-yl]ethylamine;
2-[1-(3-bromobenzenesulfonyl)-1H-pyrrolo[2,3-b]pyridin-3-yl]ethylamine;
the stereoisomers thereof; and
the pharmaceutically acceptable salts thereof.

* * * * *